United States Patent [19]

Masuda et al.

[11] 4,405,711
[45] Sep. 20, 1983

[54] ANALYSIS ELEMENT FOR IMMUNOCHEMICAL MEASUREMENT OF TRACE COMPONENTS AND METHOD FOR IMMUNOCHEMICAL MEASUREMENT USING THE SAME

[75] Inventors: Nobuhito Masuda; Shigeru Nagatomo; Yuji Mihara, all of Minami-ashigara, Japan

[73] Assignee: Fuji Photo Film Co., Ltd., Kanagawa, Japan

[21] Appl. No.: 298,812

[22] Filed: Sep. 2, 1981

[30] Foreign Application Priority Data

Sep. 2, 1980 [JP] Japan .............................. 55-120599

[51] Int. Cl.$^3$ ...................... G01N 33/54; G01N 33/52
[52] U.S. Cl. ......................................... 435/4; 422/56;
422/57; 430/537; 430/631; 435/7; 435/805;
436/538; 436/544; 436/805; 436/807
[58] Field of Search .................. 23/230 B, 915; 424/8,
424/12; 435/4, 7; 430/537, 631; 422/56

[56] References Cited

U.S. PATENT DOCUMENTS

| | | | |
|---|---|---|---|
| 4,173,480 | 11/1979 | Woodward | 430/537 X |
| 4,268,623 | 5/1981 | Sera | 430/631 X |
| 4,331,444 | 5/1982 | Mihara | 23/230 B |
| 4,337,063 | 6/1982 | Mihara | 23/230 B |
| 4,337,065 | 6/1982 | Hiratsuka | 23/230 B |

Primary Examiner—Sidney Marantz
Attorney, Agent, or Firm—Sughrue, Mion, Zinn, Macpeak and Seas

[57] ABSTRACT

In a method of assay for a trace component such as antigen, antibody or enzyme utilizing immunochemical reaction or enzyme reaction in combination with photographic detection system comprising measuring optical density of a silver image formed in proportion to the antigen, antibody or enzyme to be measured, a novel analysis sheet comprising a support having provided thereon, in succession, a water absorbing layer and a silver halide emulsion layer is employed. The analysis sheet essentially increases the amount of water absorbed so that the analysis sheet is extremely effective for improving detection sensitivity.

3 Claims, No Drawings

ANALYSIS ELEMENT FOR IMMUNOCHEMICAL MEASUREMENT OF TRACE COMPONENTS AND METHOD FOR IMMUNOCHEMICAL MEASUREMENT USING THE SAME

BACKGROUND OF THE INVENTION

1. Field of the Invention

This invention relates to an analysis element for measuring a photographically active substance to be measured or a compound labelled with a photographically active substance which is employed for a method of measuring a trace amount of a compound labelled with the photographically active substance by the use of the photographically active substance and silver halide in combination, and to a method for immunochemical measurement of a trace component using the same.

2. Development of the Invention

As methods for measuring a trace component utilizing the combination of a photographically active substance and silver halide, the following methods can be exemplified: for example, methods in which a spectral sensitizer is employed as the photographically active substance—which have been previously proposed by the present inventors—are as follows:

(I) A method for immunologically measuring trace components which comprises:
  competitively reacting an antigen or antibody labelled with a spectral sensitizer and an antigen or antibody to be measured with an antibody or antigen which specifically reacts with the antigen or antibody,
  bringing either the thus formed dye-labelled antigen-antibody reaction product or the unreacted antigen or antibody into contact with silver halide,
  exposing the same to light having a spectrally sensitizing wavelength corresponding to the spectral sensitizer,
  developing the exposed silver halide, and,
  measuring the resulting optical density of the developed silver or colored dye;

(II) A method for quantitatively measuring a trace enzyme which comprises:
  using a synthetic substrate containing a substrate structure to be specifically contacted with an enzyme to be measured and labelled with a spectral sensitizer,
  bringing either the reaction product containing the spectral sensitizer formed by enzyme reaction between the synthetic substrate and the enzyme to be measured or the unreacted synthetic substrate into contact with silver halide,
  exposing the same to light having a spectrally sensitizing wavelength of the spectral sensitizer, and,
  measuring the resulting optical density of the developed silver or colored dye;

(III) A method for detecting the location or distribution of a corresponding antibody or antigen or its receptor in tissue, utilizing the same dye labelled antigen or antibody as used in (I) above, in combination with silver halide.

In the case where the photographically active substance is a fogging agent, trace components can be measured in the same manner as above, except that the exposure procedure is omitted.

As a method for measuring trace components utilizing specificity in the antigen-antibody reaction shown in (I) and (III), radioimmunoassay (RIA) is known. The basic principles of RIA corresponding to, e.g., (I), are as foolows.

That is, the reaction of a substance marked (labelled) with a radioactive isotope (RI) in a given amount and a substance having a specific binding affinity thereto in a given amount results in a bound product of both of these components, while a part of the labelled substance remains in an unbound or unreacted free state. The reaction proceeds based on the laws of mass action in general, and, therefore, when an unlabelled substance is added to the reaction system, binding with a limited amount of binding protein is decreased and a certain relationship (calibration curve) can be established therebetween. As a result, an amount of an unknown substance can be determined from the calibration curve if the bound substance and the labelled substance in the free state are separated and either one or both are measured with respect to the RI amount.

Due to the high sensitivity and the simplicity of RIA, RIA is particularly applicable to the measurement and inspection of trace amounts of proteins in blood and hormones. Details thereon are given in, e.g., Kumahara and Shizume, *NEW RADIOIMMUNOASSAY*, pages 3 to 10 (1977), published by Asakura Publishing Co., Ltd., *KISO SEIKAGAKU JIKKENHO* (Basic Biochemical Experiment), (6), Biochemical Assay (1967), published by Maruzen Co., Ltd.

However, RIA is subject to several disadvantages due to the use of RI labelling substances ($^{125}I$, $^{131}I$, etc.) which must have high specific radioactivity to maintain immune activity and must be of high purity. For these reasons, RIA involves the danger of radiation exposure and it is necessary to use expensive and unstable labelling substances which cannot be used for extended periods of time. In addition, special installations, equipment and personnel qualified to deal with radiation are required. Finally, after RIA, disposal of radioactive waste material and the ensuing pollution problems are encountered.

Other methods for measuring the activity of an enzyme as a trace component are also known.

For example, there are: a turbidimetry method which comprises tracing the decrease in turbidity due to enzyme reaction using a suspension of a high molecular weight substrate; an absorptiometric method which comprises decomposing a high molecular weight substrate, precipitating undecomposed substrate, recovering it and then measuring soluble matter by an absorbance measurement; a method for quantitative measurement which comprises binding a dye or fluorescent substance to a high molecular weight substrate, effecting enzyme reaction to decrease the molecular weight of the dye or fluorescent substance, and measuring the dye or fluorescent substance separated; a method of quantitative measurement which comprises using a substrate which is designed to change in absorption spectrum, form a color or form a fluorescent substance, based on a splitting-off or change in a part of the substrate after enzyme reaction, and measuring the resulting absorbancy or fluorescent intensity, etc. (*SEIKAGAKU JIKKEN KOZA* (Lectures on Biochemical Experiments), vol. 5, Study on Enzymes, edited by the Biochemical Association, Japan, published by Tokyo Kagaku Dojin, 1979).

Most of these methods quantitatively determine an amount of enzyme on the order of $\mu g/ml$. Even utilizing a type of substrate releasing a fluorescent substance (e.g., derivatives of coumarine, umbelliferone, etc.), which is recognized to be most sensitive among these methods, it is only possible to measure an enzyme quantity on the order of ng/ml.

The importance of quantitative measurement of enzyme traces in blood or body fluids, the distribution of the enzymes in the living body, the amount excreted in urine, etc., has increased, and RIA has begun to be put in practice in the areas where one cannot measure activity according to the other methods above described. In addition to the problems described above, the RIA method has the following shortcomings:

(1) There is the possibility that the activity which is a functional characteristic of an enzyme is not correctly reflected because of immunoassay.

(2) There is the possibility that analogous enzymes and precursors having a similar antigenic site might be included in the analytical data.

(3) In the case where an enzyme to be measured, for example, an enzyme in an antigen or antibody labelled with the enzyme used for enzyme immunoassay, is conjugated with another compound and is not present in free form, it is difficult to prepare an antibody and design for a measurement method is practically difficult.

For these reasons, it has been desired to develop a method for the immunological examination of trace components or measurement of enzyme activity which is stable and provides sufficient sensitivity without using any isotope.

The inventors have discovered a method for the measurement of trace components with high sensitivity applicable to immunological examination and enzyme immunoassay using a photographically active substance, e.g., a spectral sensitizer, a fogging agent, etc., in combination with silver halide. Details of immunological examination are described in U.S. Ser. Nos. 126,920 and 126,919, both filed Mar. 3, 1980.

The invention will now be described with reference to the case wherein a spectral sensitizer is employed as the photographically active substance.

When a trace component to be measured as in (I) described above is, e.g., an antigen or antibody, the method is practiced as follows.

That is, the immunochemical measurement method comprises:

competitively reacting an antigen or antibody labelled with a spectral sensitizer and a testing sample containing an antigen or antibody to be measured with an antibody or antigen which specifically reacts with the respective antigen species or antibody species, bringing either the thus formed reaction product of the unreacted matter into contact with a silver halide light sensitive material, exposing the same to light having a wavelength which the spectral sensitizer absorbs, developing the exposed silver, and, quantitatively measuring the antigen or antibody based upon the optical density of the resulting silver image or the color density obtained.

Further, in the case where a trace component to be measured as in (II) described above is an enzyme, the method is practiced as follows.

That is, the method comprises, in the measurement of enzyme activity;

using a synthetic substrate containing at least one spectral sensitizer structure for photographic use, i.e., an organic dye structure ② which has an absorption region at a longer wavelength (preferably, longer than 500 nm) than the absorption wavelength inherent to silver halide and which spectrally sensitizes silver halide grains by contact with (adsorption to) the silver halide grains and at least one structure ① to be specifically contacted with the enzyme to be measured, bringing either the reaction product containing the spectral sensitizer structure ② formed by the enzyme reaction or the unreacted synthetic substrate with a silver halide light-sensitive material, exposing the same to light at a wavelength region which the spectral sensitizer sensitizes, developing, and, measuring the quantity of the developed silver or the colored dye as optical density.

Method (II) above has also been proposed by the present inventors (see copending application Ser. No. 298,814 filed Sept. 2, 1981).

The term "synthetic substrate" used herein refer to a substrate synthesized in the laboroatory as opposed to substrates derived from living tissues and is recognized in the art (see Japanese Patent Application OPI 52691/77). In the syntehtic substrate, structure ① generally comprises a site to be catalytically affected by an enzyme to be measured (in other words, a site to be catalytically, e.g., cleaved, with the enzyme) and a site to be specifically recognized by the enzyme (i.e., a recognition site or binding site) and thus specifically contacted with the enzyme to be measured.

The enzymatic reaction which occurs in Method (II) of this invention can be illustrated as shown below.

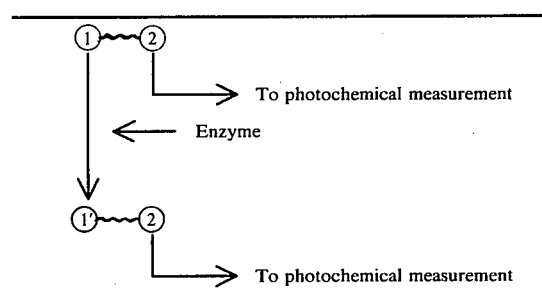

① : structure ①
② : structure ②
①' : functionally changed from ① on contact with enzyme
①〜② : unreacted synthetic substance
①'〜② : reaction product of enzymatic reaction
〜 : linkage directly linking ① and ② or indirectly via linking group ③

More specifically, structure which is present in the synthetic substrate used in the method of the present invention and specifically contacted with an enzyme to be measured is generally composed of a site to be contacted with the enzyme such as a peptide bond (acid amide bond), an ester bond, a phosphate bond, a glucoside bond for, e.g., hydrolase; or an amino group, a carboxy group, etc. for, e.g., transferase; and a site to be recognized by the enzyme (binding site) such as an amino acid residue, sugar, a nucleic acid base, etc. These are described with regard to respective enzymes described later in more detail as substrate structures corresponding to substrate specifities of enzymes in *DATA BOOK OF BIOCHEMISTRY*, first and second separate volumes (1979 and 1980), edited by the Biochemical Association, Japan, published by Tokyo Kagaku Dojin and Paul. D., Boyer et al. *The Enzyme*, vols. I, III, IV and V, 1971, published by Academic Press.

The synthetic substrate used in this invention refers to a substrate comprising linking thereto at least one structure ① corresponding to the aforesaid substrate specificity and at least one spectral sensitizer structure ② which will be later explained. Requirements for the linking are that ① enzyme reactivity not be inhibited and ② spectral sensitizing capability not be lost by the linking.

In addition to (I) and (II) described above, the method of the present invention is also applicable to the determination of the distribution state of components in the living body in tissue, such as receptor assay using the labelled antigen or antibody (receptor assay using, e.g., radioisotopes is described in detail in *RADIOIMMUNOASSAY*, Second series, edited by Minoru Irie, Chapter 12, published by Kodansha Publishing Co., Ltd.) and can be utilized for the quantitative measurement of various components in the living body, drugs, trace components such as enzymes or the like.

For measurement of trace components, an analysis sheet conventionally used, i.e., an analysis sheet comprising a support and a light sensitive silver halide emulsion layer (hereafter referred to as an "emulsion layer") has been employed in the prior art. However, contact of a trace component(s) labelled with a photographically active substance with silver halide—required in the present invention—was not sufficient with the prior art analysis sheet having such a characteristic feature. Therefore, it is necessary to enhance detection sensitivity, reproducibility, etc., in order to achieve highly sensitive measurement of trace components.

SUMMARY OF THE INVENTION

An object of the present invention is to provide an analysis element for measurement (hereafter referred to as an "analysis sheet") which provides high sensitivity and good reproducibility in a quantitative measurement method for a photographically active substance and a compound labelled with the photographically active substance using silver halide, which is employed as the detection method common to the above described, e.g., immunological examination of trace components, quantitative measurement of an enzyme, etc., and to provide a method for examination using the same.

Another object of the present invention is to provide an analysis sheet which enables one to quantitatively determine a trace component(s) in the living body in a simple and rapid manner.

A further object of the present invention is to provide a method for examining a trace component(s) in a simple manner, using an analysis sheet.

As a result of extensive investigations, the inventors have discovered that an analysis sheet having a layer structure described below is extremely effective for improving detection sensitivity of a trace component(s) labelled with the photographically active substance (a substance capable of activating silver halide) in the two methods, etc. described above, e.g., a spectral sensitizer, a fogging agent.

That is, the analysis sheet in accordance with the present invention is an analysis sheet for measurement of a trace component characterized by providing a water absorbing layer and a light sensitive silver halide layer, in this order, on a support. In this case, the water absorbing layer essentially increases the amount of water absorbed, and it is preferred that the water absorbing layer be located between the light sensitive silver halide emulsion layer (hereafter referred to as an "emulsion layer") and the support.

The water absorbing layer is essentially insensitive to light and preferably is swellable.

Further, a layer(s) other than the water absorbing layer may also be present between the emulsion layer and the support.

Further, the measurement method of this invention is, in a method for immunologically examining a trace component by labelling an antigen or antibody with a photographically active substance, a method for immunological examination of a trace component using an analysis sheet for measurement of the trace component comprising a support having provided thereon a water absorbing layer and having further provided a silver halide layer on the water absorbing layer.

Further, the measurement method of this invention is a method for examination of a trace enzyme using an analysis sheet for measurement of a trace component comprising a support having provided thereon a water absorbing layer and having further provided a silver halide layer on the water absorbing layer, in the measurement method which comprises:

using a synthetic substrate containing at least one structure ① to be specifically contacted with an enzyme to be measured and at least one spectral sensitizer structure or a fogging agent structure ② in the same molecule thereof, bringing either the reaction product containing the spectral sensitizer structure or fogging agent structure formed by enzyme reaction between the synthetic substrate and the enzyme to be measured or the unreacted synthetic substrate in contact with silver halide, exposing the same to light having a wavelength which the corresponding spectral sensitizer used absorbs, followed by development, when the synthetic substrate containing the spectral sensitizer is used, and when the synthetic substrate containing the fogging atent is used, developing the same without performing exposure, and, measuring the quantity of the enzyme from the blackened density or/and colored dye density.

PREFERRED EMBODIMENTS OF THE INVENTION

It is preferred that the water absorbing layer used in the analysis sheet of this invention be composed of, e.g., a porous membrane, a filter paper, a fiber, etc., or a binder comprising gelatin and/or a polymer and, it is preferred that the water absorbing layer be easily set (gelled) by cold air after coating. From this viewpoint, it is preferred to use at least 50 wt% of gelatin based on the total weight of binder when a mixture of gelatin and a polymer is used as the binder. To further increase the water absorption rate of the water absorbing layer, other polymers can also be effectively employed. Further, the water absorbing layer can also contain an antifogging agent, a dye, a surface active agent, and the like which are also additives for conventional silver halide emulsion layer.

It is preferred that the water absorbing layer of this invention have a thickness of from 1 to 100μ. If the layer is thinner, a sufficient water absorption rate cannot be effected. Further, in the case of using a flexible material as the support, problems such as sailing, etc., become serious when thickness is overly large, and, therefore, thickness is preferably in the range of from about 1 to about 40μ, more preferably about 4 to about 40μ, most preferably about 5 to 20μ.

The water absorbing layer can also contain, in addition to gelatin or polymers, silver halide and additives for conventional silver halide light sensitive materials, e.g., an anti-fogging agent, a dye, a surface active agent, colloidal silver and the like.

As gelatin employed for the water absorbing layer, conventional lime-treated gelatin, acid-treated gelatin, enzyme-treated gelatin obtained by treating lime- or acid-treated gelatin further with an enzyme, gelatin derivatives obtained by further treating these gelatins chemically, e.g., phthalated gelatin; grafted gelatin obtained by graft-polymerizing a monomer on such gelatins, etc., can be employed singly or in combination by mixing them in optional propertions.

It is preferred that polymers used in the invention be easily swellable and sparingly soluble in water; typical examples of such polymers are albumin, agar, gum arabic, alginic acid, etc.; hydrophilic homopolymers obtained by polymerizing a monomer of a polymerizable vinyl compound such as vinyl alcohol, vinyl pyrrolidone, acrylamide, acrylic acid, methacrylic acid, styrene, sulfonic acid styrene, methyl methacrylate, etc., or a hydrophilic copolymer thereof; cellulose compounds (e.g., hydroxyethyl cellulose, carboxymethyl cellulose, dextran, etc.), water soluble starch, etc. If necessary or desired, a hardener can also be added thereto render the same less soluble.

As hardeners employed herein, many hardeners which are known in the photographic art are effectively used. In more detail, compounds as described in *The Theory of the Photographic Process*. 4th ed., T. H. James, 1977, published by Macmillan Publishing Co., Ltd., pages 78 to 84, can be effectively employed.

The analysis sheet of this invention can further comprises a protective layer, a separating layer, a filter layer, etc., depending upon necessity or preference. The protective layer is composed of, e.g., gelatin or a synthetic or semisynthetic polymer and is generally provided on the emulsion layer.

As the separating layer, layers disclosed in Japanese Patent Application No. 124514/79 can also effectively be used in this invention.

If desired or necessary, an optical filter layer can also be provided in the analysis sheet of this invention.

Further, a neutralizing layer and a temperature-compensating polymer layer can also be provided in the analysis sheet of this invention, if necessary. By the provision of such layers, variations in the density of developed silver or colored dye due to changes in processing temperature can be substantially eliminated, even if development processing does not proceed at a constant temperature when the analysis sheet is developed. More specifically, development can be conducted in the presence of a coated layer composed of an acidic polymer layer as disclosed in, e.g., U.S. Pat. Nos. 3,362,819 and 4,028,103, and a temperature-compensating polymer layer as described in U.S. Pat. Nos. 4,056,394 and 4,061,496 and Japanese Patent Application OPI 72622/78, in combination.

The analysis sheet of this invention can be obtained by coating the aforesaid water absorbing layer, silver halide emulsion layer, protective layer and/or separating layer in succession or simultaneously on a support such as a cellulose acetate layer, a polyester layer, a paper sheet laminated with polyethylene, which is surface treated for purpose of preventing peeling between the support and a coated layer provided thereon. In this case, the support, water absorbing layer and silver halide emulsion layer are mandatory but the protective layer and separating layer can be omitted.

Further, in the analysis sheet of this invention, a gelatin and/or polymer layer can be provided at the back surface of the support, for purpose of preventing curling under high humidity or low humidity.

The emulsion layer provided in the analysis element of this invention is a layer containing silver halide. Specific examples of silver halides useful in this invention include silver chloride, silver chlorobromide, silver bromide, silver iodobromide, silver chloroiodobromide, silver chloroiodide, silver iodide, etc.

These silver halides can be emulsion dispersed or suspended in a hydrophilic colloid binder solution or can be coated on a support without any binder (e.g., a silver halide layer can be directly formed on a support by vacuum deposition, sputtering, etc.). The silver halide layer in this invention can be a single layer or, if desired or necessary, a plurality of two or more layers.

The amount of silver halide contained in the silver halide layer used for this invention is preferably in the range of from about 0.5 to 6.0, more preferably about 1.5 to about 4.5, expressed as an optical density after development processing.

Silver halide as is disclosed in Japanese Patent Applications OPI 23963/79 and 23964/79 can be used as the silver halide in the silver halide layer used in this invention. The silver halide can be prepared in a conventional manner, e.g., by a single jet method, a double jet method, or a combination thereof. In more detail, useful preparation methods of silver halide emulsions are described in, e.g., Trivelli and Smith, *The Photographic Journal*, vol. 79, pp. 330 to 338 (1939), C. E. K. Mees, *The Theory of the Photographic Process*, 1966, published by Macmillan Co., Ltd., Glafkides, *Photographic Chemistry*, vol. I, pp. 327 to 336, published by Fountain Press, etc.

The grain size of the silver halide in an emulsion(s) employed in this invention is conventional or smaller. It is thus generally preferred that the average grain size be 0.04 to 4 microns (e.g., by measurement of number average by the projected area method).

The silver halide emulsions employed in this invention are not required to be chemically ripened but generally are chemically sensitized in a conventional manner, for example, by gold sensitization (as disclosed in U.S. Pat. Nos. 2,540,085, 2,597,876, 2,597,915 and 2,399,083, etc.), by sensitization with metal ions of Group VIII of the Periodic Table, by sulfur sensitization (as disclosed in U.S. Pat. Nos. 1,574,944, 2,278,947, 2,440,206, 2,410,689, 3,189,458 and 3,415,649, etc.), by reduction sensitization (as disclosed in U.S. Pat. Nos. 2,518,698, 2,419,974 and 2,983,610, etc.), or by a combination thereof.

Specific examples of chemical sensitizers include sulfur sensitizers such as allylthio carbamide, thiourea, sodium thiosulfate, cystine, etc.; noble metal sensitizers such as potassium chloroaurate, aurous thiosulfate, potassium chloropalladate, etc.; reduction sensitizers such as stannous chloride, phenylhydrazine, reductone, etc.; polyoxyethylene derivatives as described in British Pat. No. 981,470, Japanese Patent Publication 6475/56 and U.S. Pat. No. 2,716,062, etc.; polyoxypropylene derivatives, quaternary ammonium-containing derivatives, etc.

Silver halide emulsions which are employed in this invention can also contain suitable antifoggants and stabilizers. For example, specific antifoggants and stabilizers include thiazolium salts as described in U.S. Pat. Nos. 2,131,038 and 2,694,716, etc.; azaindenes as described in U.S. Pat. Nos. 2,886,437 and 2,444,605, etc.; urazoles as described in U.S. Pat. No. 3,287,135, etc.; sulfocatechols as described in U.S. Pat. No. 3,236,652, etc.; oximes as described in U.S. Pat. Nos. 2,403,927, 3,266,897 and 3,397,987, etc.; nitron; nitroindazoles; polyvalent metal salts as described in U.S. Pat. No. 2,839,405, etc.; thiuronium salts as described in U.S. Pat. No. 3,220,839, etc.; salts of palladium, platinum and gold as described in U.S. Pat. Nos. 2,566,263 and 2,597,915, etc.

Silver halide emulsions which are used in this invention can also contain, if desired, one or more developing agents (e.g., hydroquinones, catechols, aminophenols, 3-pyrazolidones, ascorbic acid or derivatives thereof, reductones, phenylenediamines, etc.), or combinations of these developing agents. The developing agents can be incorporated into a light sensitive emulsion and/or other suitable layers (e.g., a hydrophilic binder layer) or into a photographic element. The developing agents can be incorporated using a suitable solvent or in the form of a dispersion as described in U.S. Pat. No. 2,592,368 or French Pat. No. 1,505,778.

Silver halide emulsions employed in this invention can contain coating aids such as saponin, alkylaryl sulfonates as described in U.S. Pat. No. 3,600,831, etc., amphoteric compounds as described in U.S. Pat. No. 3,133,816, etc. and can further contain antistatic agents, plasticizers, fluorescent whitening agents, developing accelerating agents, air antifogging agents, color toning agents, etc.

As the silver halide emulsion(s) used in this invention, gelatino silver halide emulsions are generally employed but this is not mandatory. For example, instead of gelatin, substances which do not have a harmful influence on the light sensitive silver halide emulsion, such as albumin, agar agar, gum arabic, alginic acid, acylated gelatin (e.g., phthalated gelatin, malonated gelatin, etc.), a homopolymer of a hydrophilic vinyl compound (e.g., vinyl alcohol, vinylpyrrolidone, acrylamide, styrene sulfonic acid, acrylic acid, etc.) or copolymers containing these vinyl compounds, cellulose compounds (e.g., hydroxyethyl cellulose, carboxymethyl cellulose, dextrin, etc.), water soluble starch, etc., can also be employed.

Photographic emulsion layers of photographic light sensitive materials used in this invention can further contain color image-forming couplers, that is, compounds capable of forming dyes by reaction with the oxidation product of an aromatic amine (normally a primary amine) developing agent (hereafter referred to as a coupler). It is preferred that the coupler be non-diffusible and comprise a hydrophobic group(s) called a ballst group(s) in the molecule thereof. The coupler(s) can be four-equivalent or two-equivalent to silver ions. In addition, the photographic emulsion layers can also contain colored couplers having a color correction effect or couplers releasing a development inhibitor upon development (DIR couplers). The couplers also can be couplers where the product of the coupling reaction is colorless.

To form the silver halide layer of the analysis of this invention, conventional techniques in the photographic art can be utilized and details are described in *COATING TECHNOLOGY*, Yuji Harazaki, published by Asakura Publishing Co., Ltd., 1972, etc. For coating the silver halide emulsions, a dip coating method, a roller coating method, a curtain coating method, an extrusion coating method, etc. can be employed.

Other layers such as the water absorbing layer, auxiliary layers, etc., can be provided in a similar manner.

Upon coating, coating aids can be employed. Examples thereof are non-ionic surface active agents such as saponin (steroid type), polyalkylene glycol alkylamines or amides, polyethylene oxide adducts of silicone, glycidol derivatives (e.g., alkenylsuccinic acid polyglycerides, alkylphenol polyglycerides), aliphatic acid esters of polyvalent alcohols, alkyl esters, urethanes or ethers of sugars, etc.; anionic surface active agents containing acidic groups such as carboxy, sulfo, phospho, sulfato, phosphato, etc., groups such as triterpenoid type saponin, alkyl carbonates, alkyl sulfonates, alkylbenzene sulfonates, alkylnaphthalene sulfonates, alkyl sulfates, alkyl phosphates, N-acyl-N-alkyltaurines, sulfosuccinates, sulfoalkyl polyoxyethylene alkylphenyl ethers, polyoxyethylene alkyl phosphates, etc.; amphoteric surface active agents such as amino acids, aminoalkyl sulfonates, aminoalkyl sulfates or phosphates, alkyl betaines, amine imides, amine oxides, etc.; cationic surface active agents such as alkyl amine salts, aliphatic or aromatic quaternary ammonium salts, heterocyclic quaternary ammonium salts such as pyridinium or imidazolium, etc., phosphonium or sulfonium salts containing an aliphatic or heterocyclic ring, etc.

As a support for the analysis element of this invention, flexible supports such as a plastic film, paper, cloth, etc. or rigid supports such as glass, porcelain, metal, etc. can be used. Useful examples of flexible supports include a film composed of semisynthetic or synthetic high molecular weight substances such as cellulose nitrate, cellulose acetate, cellulose acetate butyrate, polystyrene, polyvinyl chloride, polyethylene terephthalate, polycarbonate, etc.; a baryta paper layer, a paper sheet having coated thereon or laminated with α-olefinic polymers (e.g., polyethylene, polypropylene, ethylenebutene copolymers, etc.), or the like.

The surfaces of these supports can be subjected to a subbing treatment for improving adhesion to the silver halide layer. Further, a corona discharge, UV radiation or a flame treatment can also be performed, prior to or after the subbing treatment.

The spectral sensitizer for photographic use employed for the sensitizer-labelled substance utilized in this invention, for example, for labelling a trace component such as an antigen or antibody, a synthetic substrate for measuring enzyme activity, etc., possesses the capability to impart spectral sensitization to silver halide. Such spectral sensitizers are known as spectral sensitizers for photographic light sensitive materials and include, e.g., cyanine dyes, merocyanine dyes, hemicyanine dyes, styryl dyes, etc. These dyes are specifically described in *The Theory of the Photographic Process* (4th edition), edited by T. H. Jamese, 1977, published by Macmillan Co., Ltd., *Cyanine Dyes and Related Compounds*, F. M. Hamer, 1964, Interscience Publishers, etc.

In more detail, merocyanine dyes as described in U.S. Pat. Nos. 2,493,748, 2,519,001 and 2,652,330, German Pat. No. 1,177,481 and French Pat. No. 1,412,702; cyanine dyes as described in U.S. Pat. Nos. 2,238,213, 2,503,776, 2,537,880, 3,196,017 and 3,397,060, German Pat. Nos. 929,080, 1,028,718, 1,113,873, 1,163,671 and 1,177,482, French Pat. No. 1,359,683, British Pat. Nos. 840,223, 886,270, 886,271 and 904,332, Belgian Pat. No. 654,816, and Japanese Patent Publications Nos. 14112/65 and 23467/65, etc., are all effective dyes for this invention.

These dyes can also be employed in combinations of two or more thereof. For example, supersensitization including the use of dyes as described in Japanese Patent Publications Nos. 4932/68, 4936/68, 22884/68, etc. is also effective for this invention. Further, supersensitization as described in U.S. Pat. Nos. 2,947,630, 2,933,390, 2,937,089, 3,617,295 and 3,635,721, French Pat. No. 1,500,218, etc. is also effective. In this case, the supersensitizing dye combination can be mixed together with the labelled trace component, such as an antigen or antibody, or can be previously incorporated into the silver halide emulsion.

Of these spectral sensitizers, the dyes described below are particularly advantageous as the marking substances since these dyes are excellent in binding to the trace components such as an antigen, an antibody, a substrate for an enzyme, etc.

Preferred spectral sensitizers are described by reference to formulae (I), (II-1), (II-2) and (III) below, wherein unless otherwise indicated, a group of aliphatic nature (including a substituent, if any, and also including the alkyl moiety present in an alkoxy group, a dialkylamino group, etc.) generally possesses 1 to 12 carbon atoms, preferably 1 to 5 carbon atoms in total and a group of aromatic nature (including a substituent, if any, and also including the aryl moiety present in an aryloxy group, a diarylamino group, etc.) generally possesses 6 to 18 carbon atoms, preferably 6 to 11 carbon atoms.

(1) Cyanine dyes of formula (I) below containing at least one of a mercapto group, an amino group, a hydroxy group or a carboxy group, in the heterocyclic nucleus thereof:

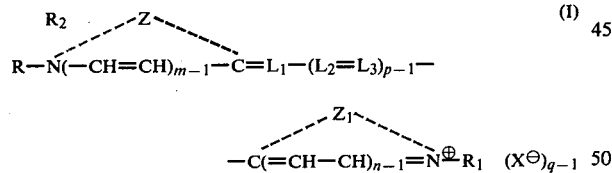

wherein m and n each represents 1 or 2; p represents 2 or 3; q represents 1 or 2; $L_1$, $L_2$ and $L_3$, which may be the same or different from each other, represents a methine group (which may be substituted with an alkyl group, a halogen atom, an aryl group, etc.); Z and $Z_1$ each represents a non-metallic atomic group necessary for completing a 5- or 6-membered nitrogen-containing heterocyclic nucleus, which may be the same or different; R and $R_1$, which may be the same or different, each represents a substituted or unsubstituted alkyl alcohol residue, $R_2$ is a substituent for Z and represents a hydrogen atom or, —$P_i$—$Q_j$—COOH wherein P represents

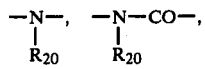

—O—, —S— or —CO—; $R_{20}$ represents a hydrogen atom or an alkyl group having 1 to 8 carbon atoms which may be substituted; Q represents an alkylene group having 1 to 10 carbon atoms which may be substituted, an arylene group which may be substituted, an aralkylene group, an alkarylene group, a dipeptide residue or a tripeptide residue; i and j each represents 0 or 1 which may be the same or different; and W represents a mercapto, amino, hydroxy or carboxy group.

At least one of R, $R_1$, $R_2$ and $Z_1$ contains at least one group selected from the class consisting of a mercapto, amino, hydroxy and carboxy groups, preferably at least one carboxy group.

Of these, particularly preferred cyanine dyes are those wherein $R_2$ alone contains a carboxy group.

(2) Merocyanine dyes of formula (II-1) below, containing at least one of a mercapto group, an amino group, a hydroxy group and a carboxy group:

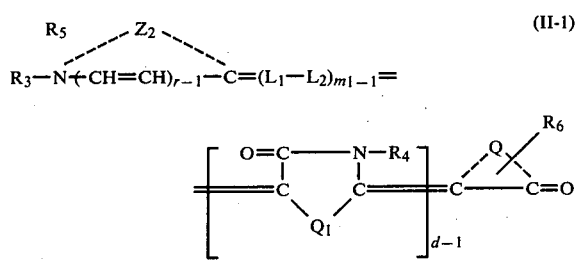

wherein
$Z_2$ has the same meaning as Z and $Z_1$;
$R_3$ and $R_4$ have the same meanings as R and $R_1$; $R_5$ has the same meaning as $R_2$; r has the same meaning as n; $L_1$ and $L_2$ are as defined above;
$m_1$ represents 2, 3 or 4;
d represents 1, 2 or 3;
$Q_1$ represents an oxygen atom, a sulfur atom or —N—$R_6$ ($R_6$ represents an aliphatic group);
Q represents a non-metallic atomic group necessary to complete a 5-membered or 6-membered nitrogen-containing heterocyclic nucleus.

In formula (II-1), at least one of $R_3$, $R_4$, $R_5$ and $R_6$ contains at least one group selected from the class containing of a mercapto group, an amino group, a hydroxy group and a carboxy group.

(3) Merocyanine dyes having a carboxy-containing substituent on the acidic nucleus and having formula (II-2), which corresponds to the merocyanine dyes of formula (II-1) wherein d is 1 and $=(L_1\text{-}L_2)_{m\text{-}1}$ is $=(CH\text{-}CH)_{p\text{-}1}$.

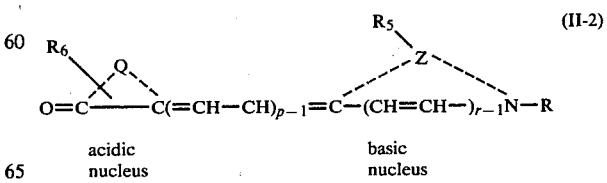

acidic nucleus      basic nucleus wherein r has the same meaning as n as hereinbefore defined, p is 2 or 3; only $R_6$ among $R_3$, $R_5$ and $R_6$ contains at least one carboxy-containing group and all other moieties are as defined for formula (II-1).

(4) Rhodacyanine dyes shown by formula (III) below, containing at least one of a mercapto group, an amino group, a hydroxy group and a carboxy group.

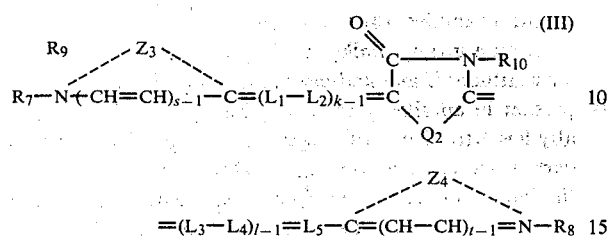

wherein
- $Z_3$ and $Z_4$ have the same meanings as $Z$ and $Z_1$; $R_7$ and $R_8$ have the same meanings as $R$ and $R_1$; $R_9$ is the same as $R_2$; s and t are the same as m and n;
- $L_1$ to $L_5$ are the same as $L_1$ to $L_3$;
- $R_{10}$ is the same as $R_4$; $Q_2$ is the same as $Q_1$;
- k and l represent 1, 2 or 3, and may be the same or different.

At least one of $R_7$, $R_8$, $R_9$, $R_{10}$ and $Q_2$ contains at least one group selected from the class consisting of a mercapto group, an amino group, a hydroxy group and a carboxy group.

Labelling of an antigen, an antibody or a synthetic substrate with the spectral sensitizer for photographic use is effected through a conventional chemical reaction. That is, the spectral sensitizer is introduced into the antigen or antibody or the structure ① to be specifically contacted with an enzyme, through a covalent bond, thus forming a labelled antigen, labelled antibody and synthetic substrate, respectively. It is preferred that the spectral sensitizer and the antigen, antibody or structure ① contain an amino group, an imino group, a mercapto group, a carboxy group, a carboxylic acid amido group or a hydroxy group and a group capable of directly reacting with such a group as functional groups which take part in the immune or enzyme reaction. In both, these functional groups may previously be present in the molecule thereof, or may be introduced through a chemical reaction. Further, the linking between these functional groups may be formed directly therebetween or formed via a suitable linking group ③. Compounds which provide linking groups ③ preferably contain the same functional groups as those for the antigen, antibody or structure ① or may contain groups other than these functional groups which can react directly with these functional groups. Further, compounds which provide linking group ③ may also contain an amino acid, peptide, polyamino acid, nucleoside, nucleotide, polynucleoside, polynucleotide moiety, etc. A method of forming the linking between these functional groups can be any of the following:

(1) Spectral sensitizers are directly reacted with the aforesaid functional groups;
(2) Spectral sensitizers and the aforesaid functional groups are reacted using an activator; and
(3) Spectral sensitizers and the aforesaid functional groups are reacted via at least one compound having a bifunctional group.

Groups which are reactive with the aforesaid functional groups of antigens or antibodies and methods for reacting the same are described in detail in, e.g., *Lectures on Experimental Biochemistry*, vol. 1 subtitled "Chemistry of Proteins", ibid., vol. 2, subtitled "Chemistry of Nucleic Acids", ibid., vol. 3, subtitled "Chemistry of Lipids" and ibid., vol. 4, subtitled "Chemistry of Sugars", all edited by the Biochemical Association, Japan, published by Tokyo Kagaku Dojin (1977); Izumiya, *PEPTIDE GOSEI* (Synthesis of Synthesis), Greenstein et al., *CHEMISTRY OF THE AMINO ACIDS*, vols. I to III (1961), John-Wiley & Sons, Inc., New York. One skilled in the art can easily perform such reactions for forming linking from knowledge in these publications.

Examples of compounds containing groups capable of reacting with the aforesaid functional groups, include e.g., activated esters, activated halogens, aldehydes, activated vinyl compounds, acid anhydrides, acid halides, thioisocyanates, isocyanates, carboxylic acids, amides, alkyl halides, nitrophenyl halides, etc. Accordingly, these functional groups can originally be present in the spectral sensitizer or can be introduced as a result of the reaction of a compound having a bifunctional group and the spectral sensitizer.

Reaction conditions for labelling vary depending upon the kind of the antigen, antibody and enzyme substrate structure ① the kind of spectral sensitizer, etc. and conditions are selected so as to not damage the biological activity of the antigen or antibody to be labelled or alter the substrate specificity to be imparted to the synthetic substrate. Accordingly, the reaction temperature is generally chosen from the range of $-40°$ to $60°$ C., preferably $-20°$ to $40°$ C.; and the reaction time from the range of from 10 mins. to 16 hrs. The reaction pressure is preferably atmospheric pressure, but can suitably chosen from the range of 1 to 20 atms. It is advantageous that water or a pH buffer solution be used as a solvent for the labelling. Organic solvents such as DM, methylene chloride, etc. can also be employed. These reaction conditions are common to reaction conditions which are generally applicable to modification of proteins or enzymes and details are described in the publications referred to above.

The amount of spectral sensitizer used for labelling varies depending upon the kind of the aforesaid substances to be labelled, but is generally in a molar ratio of 1/100 to 100 moles per 1 mole of the antigen, antibody or the enzyme substrate structure 1 preferably 1/20 to 20 times, more preferably $\frac{1}{2}$ to 2 times, same basis.

As methods for confirming completion of labelling, methods for measuring spectra such as UV, visible rays, IR, mass and NMR spectra, etc., and a method confirming labelling via disappearance of the terminal group at which the labelling substance is to be introduced, are representative. Simple tests will be enough to confirm completion of labelling. Where it is confirmed utilizing absorption spectrum, following completion of the labelling reaction, an absorption spectrum of a separated and purified product is measured; if the resulting absorption spectrum is consistent with the intrinsic absorption spectrum which a spectral sensitizer possesses, it is confirmed that the labelling reaction was effected. A further method for confirming the labelling being effected is to analyze for the presence or absence of the specific terminal groups, e.g., an amino or carboxy group(s). In case that the spectral sensitizer is introduced at the terminal amino group(s) of the spectral sensitizer, it is confirmed by the analysis of the N-terminal that completion of the labelling reaction has been effected if the corresponding amino acid(s) to an amino group(s) on which labelling is to occur are not detectable. Detailed disclosure on such N terminal analysis is described in, e.g., B. S. Hartley and V. Massey, *Biochim. Biophys. Acta*, 21, 58 (1956) (generally referred to as a Dansyl method in the art), *Archn. Biochem. Biophys.*, 22, 475 (1949) (a PTC (phenol isocyanate) method), F. Sanger, *Biochem. J.*, 39, 507 (1945) (a dinitrofluorobenzene method), etc. In a similar manner, the terminal carboxy group(s) are analyzed to check completion of the labelling reaction, details of which are given in, e.g., S. Akabori, K. Ohno and K. Narita, *Bull. Chem. Soc. Japan*, 25, 214 (1952) (generally referred to as a hydrazine decomposition method in the art), H. Matuo, U. Fujimoto and T. Tatuno, *Biochem. Biophys. Res. Communication*, 22, 69 (1966) (a tritium marking method), etc. Further, details of these terminal determination methods are also given as a review in S. B. Needleman, *PROTEIN SEQUENCE DETERMINATION*, published by Springer Verlag (Berlin), 1975.

According to the aforesaid spectral methods, after the labelling reaction is completed, the reaction product is separated and purified; thereafter the spectrum inherent to the labelled reaction product is measured to confirm the completion of labelling. For example, visible absorption spectrum is measured, and if the spectrum is identical with the inherent absorption spectrum of the spectral sensitizer used for the labelling in the visible region, taking into account solvation, association, etc., completion of the labelling is confirmed. As is described above, if the labelling is effected the terminal amino group or carboxy group of the trace component is not deteced upon analysis for the terminal group, and the effected labelling is thereby confirmed.

Also in the case of using a fogging agent as the photographically active substance, labelling is carried out in quite the same manner as in the case of using the spectral sensitizer.

The fogging agent used in this invention, i.e., substances which possess a capability of fogging silver halide, are generally known as chemical sensitizers in the photographic art, and are exemplified by sulfur containing compounds, reducible compounds, metal complexes, etc. Details on these fogging agents are described in T. H. James, *The Theory of the Photographic Process*, 4th edition, pp. 393 to 395 (1977), published by MacMillan Co., Ltd.

More specifically, useful fogging agents include:
1. Compounds containing a cyclic or acyclic thiocarbonyl group (e.g., thioureas, dithiocarbamates, trithiocarbonates, dithioesters, thioamides, rhodanines, thiohytandoins, thiosemicarbazides, or derivatives thereof)
2. Compounds containing a cyclic or acyclic thio ether group (e.g., sulfides, disulfides, polysulfides, etc.)
3. Other sulfur-containing compounds (e.g., thiosulfates, thiophosphates, and compounds derived therefrom
4. Nitrogen-containing reducible compounds (e.g., hydrazines, hydrazones, amines, polyamines, cyclic amines, hydroxylamines, quaternary ammonium salt derivatives, etc.)
5. Reducible compounds (e.g., aldehydes, sulfinic acids, enediols, metal hydride compounds, alkyl metals, aromatic compounds in dihydro form, active methylene compounds, etc.)
6. Metal complexes (e.g., four-coordinate Ni(II) or Fe(II) complexes having sulfur as a ligand, etc.)
7. Acetylene compounds
8. Others (phosphonium salts, etc.)

The order of preference in these fogging agents is, in succession of 4, 5 and 6, and then 1, 2, 7 and 3.

Further detailed description will be given with preferred examples of the compound of formula (H), wherein a group of alkyl or aliphatic nature (including a substituent if any and also including the alkyl moiety present in an alkoxy, dialkylamino group, etc.) generally has 1 to 12 carbon atoms in total, preferably 1 to 5 carbon atoms, and a group of aryl or aromatic nature (including a substituent if any and also including the aryl moiety present in an aryloxy group, an aryloxycarbonyl group, etc.) generally has 6 to 18 carbon atoms in total, preferably 6 to 11 carbon atoms, unless otherwise indicated.

Specific Examples of fogging agents which are particularly preferably employed are:

4-a. Hydrazine compounds of formula (H):

$$R-NH-NH-R^1 \qquad (H)$$

wherein R and $R^1$ are an alkyl group, an aryl group, a heterocyclic group, an acyl group, a sulfonyl group, an alkoxycarbonyl group or a group derived therefrom (R and $R^1$ may be the same or different).

Examples include hydrazine compounds such as 4-(2-formylhydrazino)phenylisothiocyanate, etc. as described in, e.g., Japanese Patent Application OPI No. 81120/78, German Pat. No. 1,597,493, Japanese Patent Publication No. 22515/71, U.S. Pat. Nos. 2,663,732, 2,618,656, 2,563,785, 2,588,982, 2,604,400, 2,675,318, 2,685,514 and 3,227,552, British Pat. No. 1,269,640, French Pat. No. 2,148,902, U.S. Pat. Nos. 4,080,207, 4,030,925 and 4,031,127, *Research Disclosure*, No. 17626 (1978, No. 176), German Patent Application OLS No. 2,719,371, Japanese Patent Application Nos. 142469/77, 125602/78 and 148522/78, Japanese Patent Application OPI No. 125062/78, etc.

4-b Hydrazone compounds of the formula:

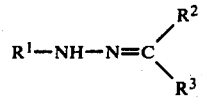

wherein $R^1$, $R^2$, $R^3$ are: an alkyl group, an aryl group, a heterocyclic group, an acyl group, a sulfonyl group, an alkoxycarbonyl group or a group derived therefrom.

Specific examples are hydrazone compounds such as 2-(2-isopropylidenehydrazino)phenyl isothiocyanate, etc., as described in U.S. Pat. Nos. 3,227,552 and 3,515,615, Japanese Patent Application OPI No. 3426/77, Japanese Patent Publication 1416/76, etc.

5-a. Aldehyde compounds of the formula:

$$R-CHO$$

wherein R is same as for $R^1$, $R^2$ or $R^3$,
e.g., a compound of the following formula:

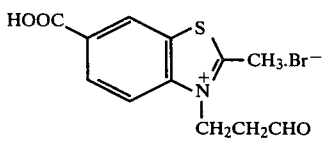

and aldehyde compounds as described in Japanese Patent Application OPI No. 9678/72, Japanese Patent Publication Nos. 19452/77, and 20088/74, etc.

5-b. Metal hydride compounds e.g., metal hydride compounds as described in Japanese Patent Publication No. 28065/70, U.S. Pat. Nos. 3,951,665 and 3,804,632, British Pat. No. 821,251, etc.

5-c. Dihydro compounds

Dihydro compounds as described in, e.g., U.S. Pat. No. 3,951,656, Belgian Pat. No. 708,563, German Pat. Nos. 1,572,125 and 2,104,161, British Pat. Nos. 1,282,084 and 1,308,753, German Patent Application OLS 1,572,140, etc.

8. Acetylene compounds of formula:

$$R-C\equiv CH$$

wherein R is the same as is defined for $R^1$, $R^2$ or $R^3$ in formulae 4-a and 4-b. e.g., a compound of the following structure:

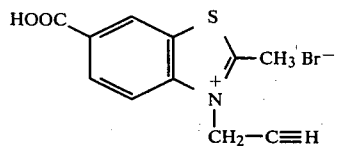

or acetylene compounds as described in German Patent Application OLS No. 2,655,870.

To separate the labelled antigen-antibody reaction product (B) from the labelled free antigen or antibody (F) in method (I) of this invention, various liquid chromatography techniques (gel filtration, ion exchange, partition chromatography, adsorption chromatography including affinity chromatography, microfilter filtration, dialysis, adsorption using cellulose, talc, dextran powder, etc., salting out, precipitation, centrifugation, crystallization, extraction, solid phase separation, etc.) can be used.

To bring either the reaction product containing spectral sensitizer structure ② or the unreacted synthetic substrate after the enzyme reaction in method (II) of this invention into contact with silver halide quantitatively, one can utilize differences in physical or chemical properties between the reaction product formed by the enzyme reaction and the unreacted synthetic substrate. For example, a difference in adsorption to silver halide can be utilized; alternatively, an appropriate separation method (e.g., ion exchange chromatography, gel filtration, adsorption chromatography, TLC, salting out, using a separation membrane, centrifugal separation, co-precipitation with a polymer, decantation, ultrafiltration, untilizing an immune reaction, adsorbents such as activated coal, etc.) can be employed.

These separation techniques are conventional in the art and details are described in, e.g., *DATABOOK ON BIOCHEMISTRY*, second separate volume, Chapter 10, edited by the Biochemical Association, Japan, published by Tokyo Kagaku Dojin, 1980, and *The Enzyme*, vols. 3, 4 and 5, Paul D., Boyer et al (1971), published by Academic Press.

In this invention, an auxiliary layer for assisting the separation described above can also be provided on the silver halide containing layer in any of the separation techniques described above to thereby compensate for such separation techniques in part or as a whole.

To bring the spectral sensitizer linked to the antigen or antibody or to the antigen-bound antibody or introduced into the synthetic substrate or the enzyme reaction product into contact with silver halide per this invention, there can be used the method of dropwise adding the aforesaid substances labelled with the spectral sensitizer to an emulsion layer containing silver halide, the method of dropwise adding the labelled substances to an emulsion solution containing silver halide, the method of otherwise contacting the labelled substances with an emulsion layer containing silver halide etc.

A preferred method is to dropwise add the labelled substances described above to an emulsion layer containing silver halide.

Trace components which can be analyzed by methods (I) (III) of this invention are typically trace components present in the living body, drugs; in addition thereto, are those amenable to analysis.

Examples of such trace components include peptide hormones (e.g., insulin, glucagon, glucagon, parathyroid hormone, carcitonin, erythropoietin, secretin, cholecystokinin, gastrin, angiotensin II, vasopressin, oxytocin, melanocyte-stimulating hormone, adrenocorticotropic hormone, growth hormone, prolactin, lutenizing hormone, follicle-stimulating hormone); non-peptide hormones (e.g., steroid hormones such as glucocorticoid, aldosterone, adrenergic androgene, estrogene, progesterone, testosterone), or other hormones such as thyroid hormones (e.g., thyroxine, triiodotyronine), cortisol, estriol, adrenaline, noradrenaline, melatonine, acetylcholine, enzymes, e.g., lysozyme, $C_1$ esterase, alkali phosphatase, pepsinogen, tripsin, kinase, virus, specific antigens, tumor antigens, e.g., α-fetoprotein, serum protein components, e.g., thyroxine-bound globulin, 2-microglobulin, IgG, IgE, IgM, IgA, human lysozyme; drugs (e.g., LSD, etc.); others (e.g., rheumaoid factor, $B_s$ antigen, $B_s$ antibody, myosin, etc.).

In preparing these trace components labelled with a spectral sensitizer, the trace components can be employed as raw materials as they are, but substances (derivatives from natural substances or synthesized substances) having an immune reactivity equivalent to these trace components, which are derived therefrom, can also be employed.

Typical examples of enzymes which can be measured in method (III) of this invention are: proteinase such as trypsin, plasmin, kallikrein, thrombin, chymotrypsin, urokinase, catepsin, streptomyces alkali protease, papain, ficin, bromerain, renin, collagenase, erastase, etc.; peptidase e.g., leucine aminopeptidase, aminopeptidase, acylaminopeptidase, carboxypeptidase, dipeptidyl peptidase, etc.; nuclease, e.g., ribonuclease A, ribonuclease $T_1$, deoxyribonuclease $A_1$, endonuclease, etc.; glycogenase including lyase type enzymes, e.g., amylase, lysozyme, glucosidase, galactosidase, mannosidase, phosphorylase, glucanase, hyaluronidase, chondroitinase, arginic acid lyase, etc.; lipase type enzymes, e.g., lipase, phospholipase, etc.; transferase type enzymes, e.g., transcarbamylase, aminotransferase, acyltransferase, phosphotransferase, etc.; lyase type enzymes, e.g., carboxylase, hydrolyase, ammonialyase, etc. These enzymes are described in *ENZYME*, edited by Masaru Funatsu, published by Kodansha Publishing Co., Ltd. (1977), *DATABOOK OF BIOCHEMISTRY*, first and second separte volumes (1979 and 1980), edited by the Biochemical Association, Japan, published by Tokyo Kagaku Dojin, and *The Enzyme*, vols. III, IV and V, Paul D., Boyer et al., 1971, published by Academic Press, etc.

The method of this invention further applies not only to enzymes present in the living body but also to enzyme analysis in general, e.g., to enzymes present in, e.g., soils, culture solutions, culture media, etc., enzymes isolated from the living body or the aforesaid substances, enzymes immobilized by various soluble or insoluble carriers, enzymes contained in antigens or antibodies labelled with these enzymes e.g., enzymes in the labelled substances in enzyme immunoassay.

In order to make the separation of the enzyme reaction product containing spectral sensitizer structure or fogging agent structure ② from the unreacted synthetic substrate in method (II) utilizing the enzyme reaction easier, particular synthetic substrates having a high molecular weight which possess the property that the reaction product containing spectral structure or fogging agent structure ② shows a reduction in molecular weight as a result of the enzyme reaction and is released or isolated (e.g., natural substrates of high molecular weight labelled with the spectral sensitizer, etc.), or immobilized substrates (e.g., substrates having the spectral sensitizer linked to carriers such as latex, glass beads, microcapsules, resins, filter paper, fibers, etc., directly or via linking group (3) described above) can also be employed.

In the case that the photographically active substance is a spectral sensitizer, exposure described below is required.

A variety of light sources can be employed for exposing the silver halide brought into contact with the spectral sensitizer. In any case, only light having a wavelength(s) that the spectral sensitizer alone absorbs is employed for exposure, excluding a wavelength in the absorption region intrinsic to silver halide. As light sources, for example, a tungsten lamp, a halogen lamp, a mercury lamp, a xenon lamp, etc. can be employed in combination with a suitable optical filter (e.g., a sharp cut filter manufactured by Fuji Photo Film Co., Ltd.). In addition, a solid laser (e.g., a ruby laser, etc.), a semiconductor laser (e.g., a lead sulfide laser, etc.), a dye laser, a gas laser (e.g., a neon helium laser, an argon laser, etc.) and the like can be advantageously employed.

In this invention, it is preferred that when a transparent film (support) having the emulsion layer thereon is exposed, exposure be performed through the support to the emulsion layer. Upon exposure, it is necessary to employ a light source having overlaid thereon an optical filter to absorb light having wavelengths in the absorption region intrinsic to silver halide, or to use light from which wavelengths in the absorption region intrinsic to silver halide have been filtered out. It is particularly preferred that exposure be performed through a light source having overlaid thereon an optical filter which mainly transmits light of wavelengths that the spectral sensitizer absorbs.

The emulsion layer exposed as described above is then processed by conventional photographic processing. That is, in the case where the emulsion(s) are coated on a support, development processing techniques as are conventionally used for processing ordinary photographic films or printing paper can be utilized. Further, photographic processing can also be effected by developing, coating or spraying processing solutions on a support having coated thereon the emulsion(s), or dipping the support in processing solutions. Further, photographic processing can also be performed by incorporating or mixing processing solutions into or with a liquid type emulsion.

The development processing temperature is generally selected between 18° and 50° C., but can be lower than 18° C. or higher than 50° C. Depending upon the purpose, any development processing forming silver images (black-and-white photographic processing) and color photographic processing comprising development processing to form color images can be used.

The optical density or degree of blackening increases with increase in processing temperature. Accordingly, it is desired that processing be performed at a constant temperature. However, instead of using constant temperature processing, a technique in which the optical density or degree of blackening is not substantially changed by using the aforesaid neutralizing layer and temperature-compensating layer in combination is also effective.

Developing solutions used in the case of black-and-white photographic processing can contain known developing agents. As such developing agents, dihydroxybenzenes (e.g., hydroquinone), 3-pyrazolidones (e.g., 1-phenyl-3-pyrazolidone), aminophenols (e.g., N-methyl-p-aminophenol), 1-phenyl-3-pyrazolines, ascorbic acid, and heterocyclic compounds comprising a condensed 1,2,3,4-tetrahydroquinoline ring and an indolene ring as described in U.S. Pat. No. 4,067,872, etc., can be used singly or as a combination thereof.

The developing agent solutions can generally contain known preservatives, alkali agents, pH buffers, antifogging agents, and, if necessary, dissolution aids, color toning agents, development accelerators, surface active agents, defoaming agents, softening agents, hardening agents, viscosity-imparting agents, etc.

"Lith" type development processing can also be applied to the photographic emulsion of this invention. The term "lith" type development processing refers to development processing which comprises, for the purpose of photographic reproduction of line images or photographic reproduction of half tone images using dots, infectious development at a low concentration of sulfite ions generally using a dihydroxybenzene(s) as a developing agent, the details of which are given in *Photographic Processing Chemistry*, Mason, 163–165 (1966).

As a special aspect of development, a developing method which comprises treating a light sensitive material in which a developing agent is contained, e.g., in an emulsion layer, in an aqueous alkaline solution can be used. Of such developing agents, hydrophobic types can be incorporated into an emulsion layer by latex dispersion, as disclosed in *Research Disclosure*, No. 169, RD-16928. Such development processing can also be used in combination with silver salt stabilization, e.g., with a thiocyanate(s).

As fixing solutions, those having compositions conventionally used in photographic processing can be employed, e.g., as fixing agents, organic sulfur compounds such as thiosulfates, thiocyanates and other organic sulfur compounds that are known as having a fixing effect can be employed. The fixing solution can also contain water soluble aluminum salts as a hardening agent.

To form dye images, again conventional methods are used. A nega-posi method (e.g., as described in *Journal of the Society of Motion Picture and Television Engineers*, vol. 61, 667-701 (1953) can also be used; further, a color reversal method which comprises developing with a developer containing a black-and-white developing agent to form negative silver images, then performing at least one overall exposure or other suitable fogging treatment and subsequently color developing to obtain positive color images can also be used; also, a silver dye bleach method which comprises exposing a photographic emulsion layer containing a dye, developing to thereby form silver images, and then bleaching the dye using the silver images as a bleaching catalyst, etc., can be used.

In general, a color developer comprises an aqueous alkaline solution containing a color developing agent. As color developing agents, known primary aromatic amine developing agents, for example, phenylenediamines (e.g., 4-amino-N,N-diethylaniline, 3-methyl-4-amino-N,N-diethylaniline, 4-amino-N-ethyl-N-beta-hydroxyethylaniline, 3-methyl-4-amino-4-ethyl-N-beta-hydroxyethylaniline, 3-methyl-4-amino-N-ethyl-N-beta-methanesulfamidoethylaniline, 4-amino-3-methyl-N-ethyl-N-beta-methoxyethylaniline, etc.) can be used.

In addition, compounds as described in L. F. A. Mason, *Photographic Processing Chemistry*, 226-229, 1966, Focal Press; U.S. Pat. Nos. 2,193,015 and 2,592,364; and Japanese Patent Application Laid Open OPI No. 48-64933, etc., can be used.

The color developer can also contain a pH buffering agent such as a sulfite, carbonate, borate and phosphate of an alkali metal, a development inhibitor or an antifogging agent such as a bromide, iodide or an organic antifogging agent, etc. The color developer can also contain, if necessary, a hard water softener, a preservative such as hydroxylamine, an organic solvent such as benzyl alcohol or diethylene glycol; a development accelerator such as polyethylene glycol, a quaternary ammonium salt or an amine; a dye forming coupler, a competing coupler, a fogging agent such as sodium borohydride, an auxiliary developing agent such as 1-phenyl-3-pyrazolidone, a viscosity imparting agent, a polycarboxylic acid type chelating agent as described in U.S. Pat. No. 4,083,723, an antioxidant as described in German Patent Application (OLS) No. 2,622,950, etc. Of course, combinations of the above materials can also be used.

The photographic emulsion layers after color development is/are usually subjected to bleaching. Bleaching can be performed with fixing at the same time or separately therefrom. Representative examples of bleaching agents include polyvalent metal compounds of iron (III), cobalt (III), chromium (VI), copper (II), etc., peroxides, quinones, nitroso compounds, etc. For example, ferricyanides, bichromates, inorganic complexes of iron (III) or cobalt (III), aminopolycarboxylic acids such as ethylenediamine tetraacetic acid, nitrilotriacetic acid, 1,3-diamino-2-propanol tetraacetic acid, etc., complexes of organic acids such as citric acid, tartaric acid, maleic acid, etc.; persulfates, permanganates; nitrosophenol, etc., can be employed. Of these, potassium ferricyanide, ethylene diamine tetraacetic acid iron (III) sodium and ethylene diamine tetraacetic acid iron (III) ammonium are particularly useful both in an independent bleaching solution and in a mono bath bleaching-fixing solution.

The bleaching or blix solutions can also contain bleach accelerators as described in U.S. Pat. Nos. 3,042,520 and 3,241,966 and in Japanese Patent Publications Nos. 45-8506 and 45-8836, etc., thiol compounds as described in Japanese Patent Application Laid Open (OPI) No. 53-65732 and other various additives.

Processing solutions used in this invention can be liquid compositions containing processing components necessary for the development of silver halide emulsions and the formation of diffusion transfer dye images in which the major portion of the solvent is water and wherein a hydrophilic solvent(s) such as methanol, methyl cellosolve, etc., can also optionally be present in addition of water.

The processing compositions should have a pH necessary for development of the emulsion layers and should contain alkali in an amount sufficient to neutralize acids (e.g., hydrogen halides such as hydrogen bromide, carboxylic acids such as acetic acid, etc.) released during various steps for developing and forming dye images. As the alkali, alkali metal or alkaline earth metal salts, e.g., lithium hydroxide, sodium hydroxide, potassium hydroxide, a calcium hydroxide dispersion, hydroxylated tetramethyl ammonium, sodium carbonate, trisodium phosphate, diethyl amine, etc., or other amines are illustrative. Preferably, the alkali is an alkali hydroxide and imparts a pH of at least 12 at room temperature, more preferably a pH of at least 14.

More preferably, the processing compositions contain hydrophilic polymers such as high molecular weight polyvinyl alcohol, hydroxyethyl cellulose, sodium carboxymethyl cellulose and the like. These polymers impart a viscosity of at least 1 poise at room temperature, preferably several hundred (500 to 600) to 1000 poise to the processing compositions to thereby not only provide uniform development upon processing but also to permit easy transfer of aqueous solvent into the light sensitive element and an image receiving element during processing, where, when the processing compositions are condensed, a non-fluid layer can be formed to assist formation of a film unit which is firmly united after processing. Such a hydrophilic polymer layer prevents, after the formation of a diffusion transfer color image is substantially complete, further transfer of colored component into the image receiving layer to thereby help prevent image changes.

In some cases, it is advantageous that the processing compositions also contain light absorbing substances such as $TiO_2$ or carbon black, pH indicators, or desensitizers as described in U.S. Pat. No. 3,579,333, in order to prevent a silver halide(s) from being fogged by an external light. In addition, the processing compositions can also contain development inhibitors such as benzotriazole. The aforesaid processing compositions can be used by encasing the same in a rupturable container as described in U.S. Pat. Nos. 2,543,181, 2,643,886, 2,653,732, 2,723,051, 3,056,491, 3,056,492 and 3,152,515, etc.

In the assay method of this invention, the labelled trace components can be used in combination with a compound represented by formula (X) below, when the photographically active substance used for labelling is a spectral sensitizer. By the use of this compound, stability of substances labelled with a spectral sensitizer, in particular, stability in an aqueous medium with the passage of time where an antigen-antibody reaction, enzyme reaction, or the like is performed, can be improved.

$$D_1-A-D_2 \qquad (X)$$

wherein $D_1$ and $D_2$ each represents a condensed polycyclic aromatic heterocyclic moiety or an aromatic hetero ring-substituted amino group, which may contain an —SO$_3$M group, wherein M is a hydrogen atom, an alkali metal or an ammonium group; —A— represents a divalent aromatic residue, which may contain an —SO$_3$M group, provided that the —A— moiety should contain an —SO$_3$M group when no —SO$_3$M group is contained in either $D_1$ or $D_2$ described above.

Preferred examples of the divalent aromatic residue represented by A are as follows:

Groups containing a sulfo group:

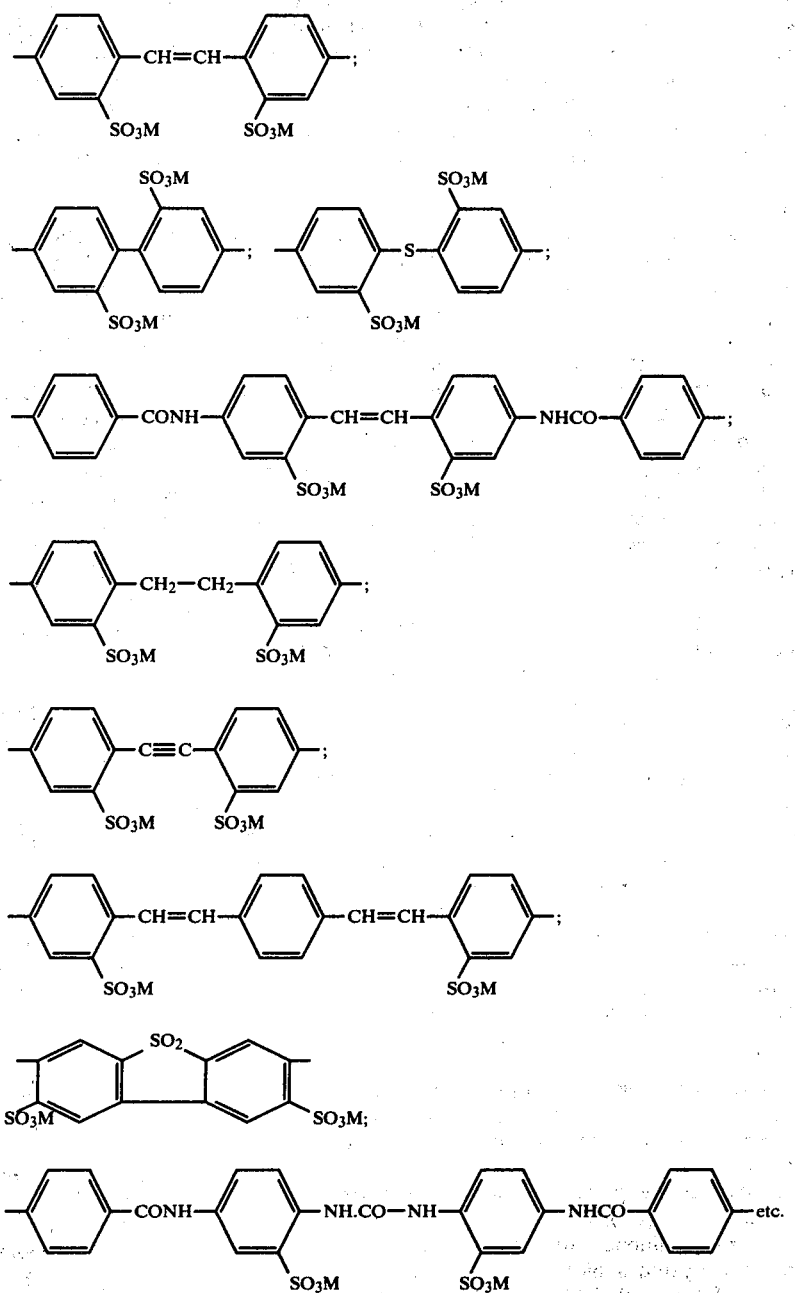

Groups free of a sulfo group:

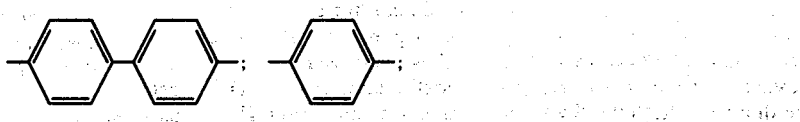

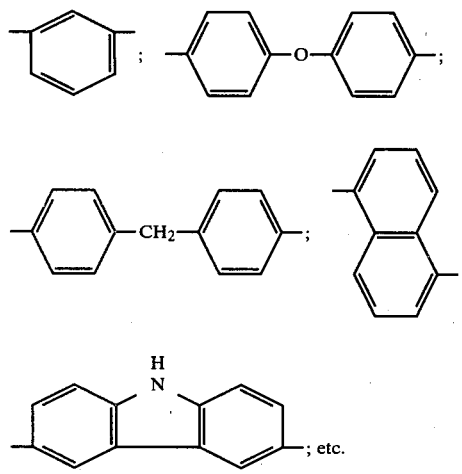

When no sulfo group is contained in A, at least one of $D_1$ and $D_2$ contains an —SO$_3$M-containing group.

Of these divalent aromatic residues, more preferred is:

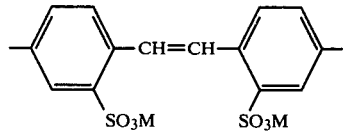

Examples of the alkali metal represented by M include sodium, potassium, etc., and examples of the halogen atom include chlorine, bromine, iodine, etc.

Of compounds represented by formula (X), particularly preferred are those represented by the following formulae (XI) and (XII), wherein an alkyl group (including the alkyl moiety contained in an alkoxy group, an alkylthio group, etc. and including a substituent thereon, if any) generally has 1 to 20 carbon atoms, preferably 1 to 12 carbon atoms and an aryl group (including the aryl moiety contained in an aryloxy group, an arylthio group, etc. and including a substituent thereon, if any) generally has 6 to 30 carbon atoms, preferably 6 to 15 carbon atoms, unless otherwise indicated.

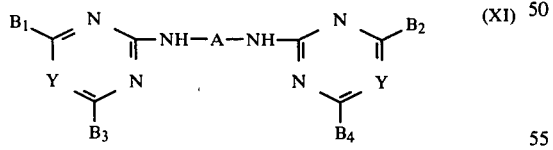 (XI)

wherein —A— has the same meaning as in formula (X); Y represents =CH—, =CB$_5$— or =N— wherein B$_5$ represents a lower alkyl group, a halogen atom, etc.; B$_1$, B$_2$, B$_3$ and B$_4$ each represents a hydrogen atom, a hydroxy group, an alkoxy group, a lower alkyl group (e.g., a methyl group, an ethyl group, etc.), an aryloxy group (e.g., a phenoxy group, an o-tolyloxy group, a p-sulfophenoxy group), a halogen atom (e.g., a chlorine atom, a bromine atom), a heterocyclic nucleus (e.g., a morpholynyl group, a piperidyl group), an alkylthio group (e.g., a methylthio group, an ethylthio group), a heterocyclylthio group (e.g., a benzothiazolylthio group), an arylthio group (e.g., a phenylthio group, a tolylthio group), an amino group, an alkylamino group or substituted alkylamino group (e.g., a methylamino group, an ethylamino group, a propylamino group, a dimethylamino group, a diethylamino group, a dodecylamino group, a cyclohexylamino group, a β-hydroxyethylamino group, a di(β-hydroxyethyl)amino group, a β-sulfoethylamino group), an arylamino group or substituted arylamino group (e.g., an anilino group, an o-sulfoanilino group, a m-sulfoanilino group, a p-sulfoanilino group, an o-anisylamino group, a m-anisylamino group, a p-anisylamino group, an o-toluidino group, a m-toluidino group, a p-toluidino group, an o-carboxyanilino group, a m-carboxyanilino group, a p-carboxyanilino group, a hydroxyanilino group, a disulfophenylamino group, a naphthylamino group, a sulfonaphthylamino group), a heterocycloamino group (e.g., a 2-benzothiazolylamino group, a 2-pyridylamino group), an aryl group ((e.g., a phenyl group), or a mercapto group; B$_1$, B$_2$, B$_3$ and B$_4$ each may be the same or different; when —A— contains no sulfo group, at least one of B$_1$, B$_2$, B$_3$ and B$_4$ should contain at least one sulfo group (which may be a free acid group or form a salt).

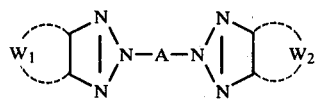 (XII)

wherein A has the same significance as in formula (X); W$_1$ and W$_2$ each represents the carbon atoms for completing a benzene ring or a naphthalene ring where the benzene ring or naphthalene ring may be substituted and at least one of these substituents, if any, should contain a sulfo group.

Specific examples of compounds represented by the above formulae (XI) and (XII) are shown below.

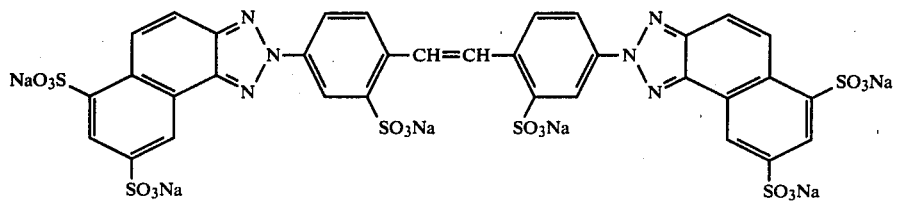

Compound 1

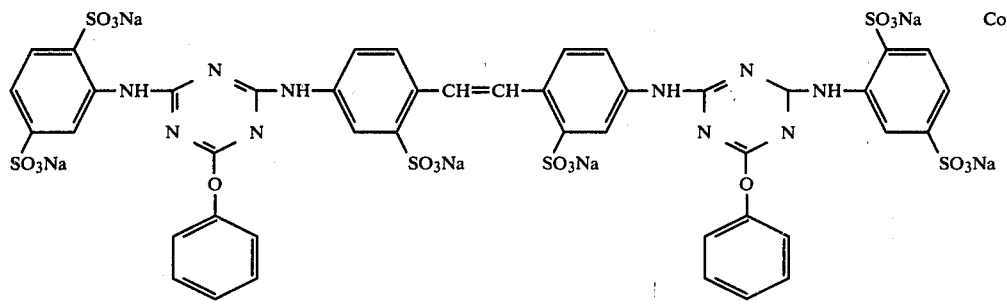

Compound 2

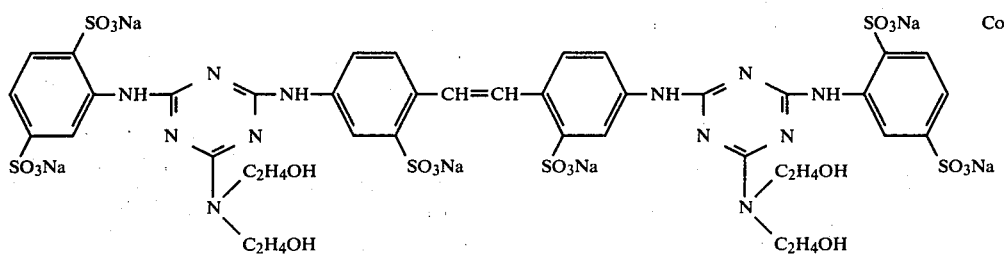

Compound 3

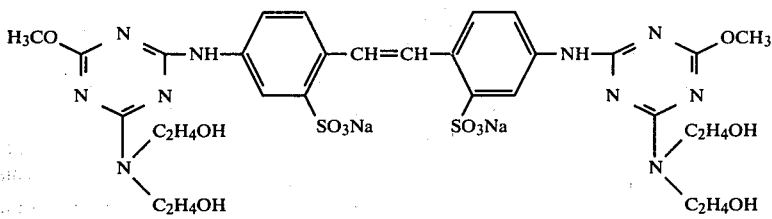

Compound 4

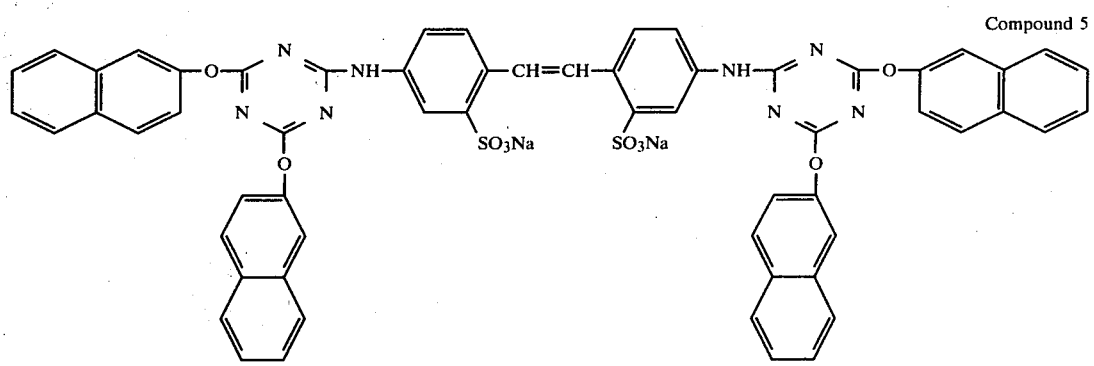

Compound 5

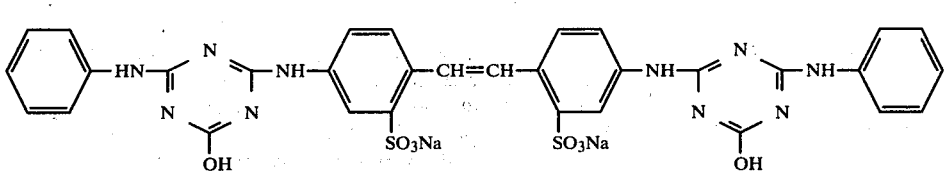

Compound 6

The compound represented by formula (X) is preferably employed in the form of a water containing solution of a 0.0001 to 1 wt% concentration, more preferably as a water containing solution of from 0.001 to 0.01 wt%.

When a spectral sensitizer is brought into contact with silver halide grains, the presence of a hydrazine compound of formula (IX) increases detection sensitivity of the silver halide.

$$R^1\text{—NH—NH—}\overset{\overset{O}{\|}}{C}\text{—}R^2 \quad (IX)$$

wherein $R^1$ is an aryl group which may be substituted, $R^2$ is a hydrogen atom, an alkyl group which may be substituted or an aryl group which may be substituted. Details and the "presence state" of such hydrazine compounds are described in copending U.S. Ser. No. 298,814 filed Sept. 2, 1981.

In order to bring the spectral sensitizer labelling substance into contact with silver halide or to absorb the spectral sensitizer to silver halide, exposing or developing, in the state where the hydrazine compound is present, the hydrazine compound can be present in a testing sample, can be previously incorporated into the silver halide light sensitive material or can be added to a developer, etc.

The amount of the compound represented by formula (IX) is generally in the range of from $10^{-8}$ to $10^{-1}$ mol/mol Ag, preferably $10^{-6}$ to $10^{-2}$ mol/mol Ag, when the hydrazine compound is incorporated into the silver halide light sensitive material.

To incorporate the compound represented by formula (IX) into the light sensitive material, methods as are conventionally used for adding additives to photographic emulsions are applicable. For example, the hydrazine compound can be added to photographic emulsions or light insensitive hydrophilic colloid solutions in the form of an aqueous solution of a suitable concentration when the compound is soluble in water, it can be added in the form of a solution obtained by dissolving the hydrazine compound in an appropriate solvent compatible with water which does not adversely affect photographic properties, e.g., selected from alcohols, glycols, ketones, esters, amides, etc. Techniques used for adding water insoluble (oil soluble) couplers to emulsions as a dispersion thereof, which are well known in the photographic art, also apply to this invention.

In the case that the hydrazine compound shown by formula IX is incorporated into a photographic pre-bath or developer or a buffer solution employed for the immune reaction, the amount thereof is generally in the range of from 5 mg. to 15 g., preferably 10 mg. to 5 g., per 1 liter of the pre-bath, developer or buffer solution.

The most preferred technique in this invention is that where the hydrazine compound is mixed with the silver halide emulsion and the mixture is coated to form an analysis element.

Further detailed description will be given with respect to the compound represented by formula (IX) wherein an alkyl or aliphatic group (including a substituent if any and also including the alkyl moiety present in an alkoxy group, a dialkylamino group, etc.) generally has 1 to 12 carbon atoms in total, preferably 1 to 5 carbon atoms, and an aryl or aromatic group (including a substituent if any and also including the aryl moiety present in an aryloxy group, an aryloxycarbonyl group, etc.) generally has 6 to 18 carbon atoms in total, preferably 6 to 11 carbon atoms, unless otherwise indicated.

The aryl group represented by $R^1$, which may be substituted, is a monocyclic or bicyclic aryl group. Examples are a benzene ring and a naphthalene ring. Particularly preferred ones are those containing a benzene ring.

The aryl group may be substituted. Preferred examples of such substituents are shown below:

(1) Straight, branched and cyclic alkyl groups, preferably containing 1 to 20 carbon atoms, such as a methyl group, an ethyl group, an isopropyl group, an n-dodecyl group, and a cyclohexyl group;

(2) Aralkyl groups, preferably monocyclic and bicyclic aralkyl groups having an alkyl moiety containing 1 to 3 carbon atoms, such as a benzyl group;

(3) Alkoxy groups, preferably containing 1 to 20 carbon atoms, such as a methoxy group and an ethoxy group;

(4) Amino groups, preferably an $-NH_2$ group and those amino groups mono- or di-substituted by an alkyl group containing 1 to 20 carbon atoms, such as a dimethylamino group and a diethylamino group;

(5) Aryloxy groups, preferably a phenoxy group;

(6) Groups represented by $A_h-X_h-(Y)_{nh}-$ (7) Groups represented by

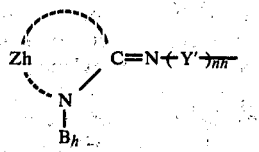

(8) Groups represented by $R^{3h}CONHNH-Ar-Y''-$.

In the formula: $A_h-X_h-(Y)_{nh}-$ as illustrated above, Group (6):

(a) $X_h$ is a divalent linking group selected from the following $x_1$ to $x_{11}$: $x_1 = -CSNH-$, $x_2 = -S-CSNH-$,

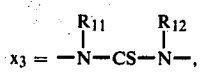

$x_4 = -CONH-$, $x_5 = -O-E-CONH-$,

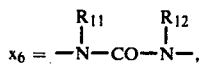

$x_7 = -NHCO-$, $x_8 = -O-$, $x_9 = -SO_2NH-$, $x_{10} = -E-NH-$, and $x_{11} = -E=N-$;

(b) Y is a divalent linking group selected from the following $y_1$ to $y_{11}$: $y_1 = -CONH-$, $y_2 = -E-CONH-$, $y_3 = -E-$, $y_4 = -E-O-E'-$, $y_5 = -E-S-E'-$, $y_6 = -SO_2NH-$, $y_7 = -E-SO_2NH-$, $y_8 = -NHCONH-$, $y_9 = -E-NHCONH-$, $y_{10} = -E-O-E'-CONH-$, and $y_{11} = -E-E'-$, wherein $R_{11}$ is a hydrogen atom, an aliphatic group (preferably, an alkyl group containing 1 to 20 carbon atoms, a cycloalkyl group containing 3 to 12 carbon atoms, or an alkenyl group containing 2 to 20 carbon atoms), or an aromatic group (preferably, a phenyl group and a naphthyl group), $R_{12}$ is a hydrogen atom or an aliphatic group represented by $R_{11}$, $R_{11}$ and $R_{12}$ may combine with each other to form a ring, with preferred examples of such ring being

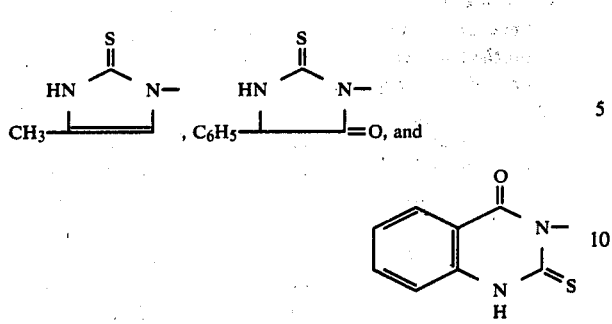

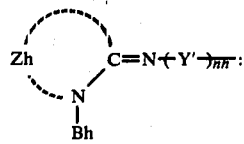

(in this case, Ah represents hydrogen),
when $R_{11}$ and $R_{12}$ do not form a ring, any one of $R_{11}$ and $R_{12}$ is a hydrogen atom, and
E and E' each represents a saturated or unsaturated divalent aliphatic group (e.g., an alkylene group, such as an ethylene group and a 1-methylpropylene group, and an alkenylene group, such as a propenylene group and a butenylene group), a divalent aromatic group (e.g., a phenylene group, a naphthylene group and a 5-amino-1,2-phenylene group), with the exception that in $y_{11}=-E-E'-$, E and E' are divalent groups different from each other and in $x_{11}=-E=N-$, E is $-(CH_2)_{mh}-CH=$ (wherein m is an integer of 0 to 2);

(c) nh is an integer of 0 or 1, and when nh is 1, particularly preferred combinations of Xh and Y are $x_3$-$y_2$, $x_7$-$y_2$, $x_8$-$y_2$, $x_{12}$-$y_3$, $x_3$-$y_7$, $x_5$-$y_9$, $x_9$-$y_9$, and $x_3$-$y_{10}$; and (d) Ah represents a straight, branched or cyclic alkyl group (preferably containing 1 to 20 carbon atoms, such as a methyl group, a propyl group, and an n-hexyl group), a monocyclic or bicyclic aryl group (e.g., a phenyl group), a monocyclic or bicyclic aralkyl group (preferably containing 7 to 26 carbon atoms, such as a benzyl group), and a heterocyclic radical.

The heterocyclic radical represented by Ah is a 5- or 6-membered ring containing therein at least one hetero atom and may be condensed with an aromatic ring, particularly a benzene ring. Particularly, a heterocyclic radical containing at least one nitrogen atom is preferred. Examples are a thiazolyl group, a benzthiazolyl group, an imidazolyl group, a thiazolinyl group, a pyridinyl group, a tetrazolyl group, a benztriazolyl group, an indazolyl group, a benzimidazolyl group, a hydroxytetrazainden-2 or 3-yl; mercapto group-containing heterocyclic groups, such as 2-mercaptobenzthiazolyl group and a 2-mercaptobenzoxazolyl group; and quaternary nitrogen atom-containing heterocyclic radicals, such as 2-methylbenzthiazolinium-3-yl, 2-(N-sulfoethylbenzthiazolinio), and N,N-dimethylbenzimidazolinium-2-yl.

The foregoing groups represented by Ah may be substituted. Examples of such substituents include:
an alkoxy group (preferably containing 1 to 18 carbon atoms, such as a methoxy group),
an alkoxycarbonyl group (preferably containing 2 to 19 carbon atoms, such as an ethoxycarbonyl group),
a monocyclic or bicyclic aryl group (e.g., a phenyl group),
an alkyl group (preferably containing 1 to 20 carbon atoms, such as a methyl group and a tert-amyl group),
a dialkylamino group (preferably containing 1 to 20 carbon atoms, such as a dimethylamino group),
an alkylthio group (preferably containing 1 to 20 carbon atoms, such as a methylthio group),
a mercapto group, a hydroxy group, a halogen atom, a carboxy group, a nitro group, a cyano group,
a sulfonyl group (preferably containing 1 to 20 carbon atoms, such as a methylsulfonyl group), and
a carbamoyl group (preferably containing 1 to 20 carbon atoms, such as a carbamoyl group and a dimethylcarbamoyl group).

In the foregoing group represented by Group (7)

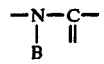

(a) Zh is a group of non-metallic atoms and combines with $$-N-C- \atop \phantom{-}|\phantom{-}\|\phantom{-} \atop \phantom{-}B\phantom{-}$$

to form a 5- or 6-membered heterocyclic ring, with suitable examples of such 5- or 6-membered heterocyclic rings being a thiazoline ring, a benzthiazoline ring, a naphthothiazoline ring, a thiazolidine ring, an oxazoline ring, a benzoxazoline ring, an oxazolidine ring, a selenazoline ring, a benzselenazoline ring, an imidazoline ring, a benzimidazoline ring, a tetrazoline ring, a triazoline ring, a thiadiazoline ring, a 1,2-dihydropyridine ring, a 1,2-dihydroquinone ring, a 1,2,3,4-tetrahydroquinoline ring, a perhydro-1,3-oxazine ring, a 2,4-benz[d]oxazine ring, a perhydro-1,3-thiazine ring, a 2,4-benz[d]thiazine ring and a uracyl ring;

(b) Bh is a hydrogen atom or a saturated or unsaturated aliphatic group [such as an alkyl group (preferably containing 1 to 20 carbon atoms, e.g., a methyl group and an ethyl group), an alkenyl group (preferably containing 2 to 22 carbon atoms, e.g., an allyl group), and an alkynyl group (preferably containing 2 to 20 carbon atoms, e.g., a butynyl group)], which may be substituted by an alkoxy group, an alkylthio group, an acylamino group, an acyloxy group, a mercapto group, a sulfo group, a carboxy group, a hydroxy group, a halogen atom, an amino group, or the like;

(c) Y' has the same meanings as described for Y in Group (6); and (d) nh is 0 or 1.

In the group represented by the formula: $R^{3h}CONHNH-Ar-Y''-$, Group (8):

(a) $R^{3h}$ is the same as $R^2$ as described hereinafter;

(b) $-Ar-$ represents a divalent aryl group, preferably a phenylene group, which may be substituted; and (c) $Y''$ is the same as Y described in Group (6), with divalent linking groups represented by $y_3$ to $y_5$ being particularly preferred.

In formula (IX), $R^2$ is a hydrogen atom, an alkyl group which may be substituted, or an aryl group which may be substituted. Substituents which can be used include a halogen atom, a cyano group, a carboxy group, and a sulfo group. Examples of such alkyl and aryl groups are a methyl group, an ethyl group, an n-propyl group, an isopropyl group, a phenyl group, a 4-chlorophenyl group, a 4-bromophenyl group, a 3-chlorophenyl group, a 4-cyanophenyl group, a 4-carboxyphenyl group, a 4-sulfophenyl group, a 3,5-dichlorophenyl group, and a 2,5-dichlorophenyl group.

Of the substituents represented by $R^2$, a hydrogen atom, a methyl group and a phenyl group (including a substituted phenyl group) are preferred, and a hydrogen atom is particularly preferred.

Preferred examples of the compounds represented by formula (IX) are described in U.S. Pat. Nos. 4,168,977 and 4,224,401 and British Pat. No. 1,558,946, Japanese Patent Application (OPI) Nos. 52050/80 and 90940/80, *Research Disclosure*, No. 17626 (Vol. 176, 1978), etc. Of these compounds, those described in U.S. Pat. Nos. 4,168,977 and 4,224,401 are particularly preferred.

Specific examples of compounds represented by formula (IX) are shown below, but this invention is not limited only thereto.

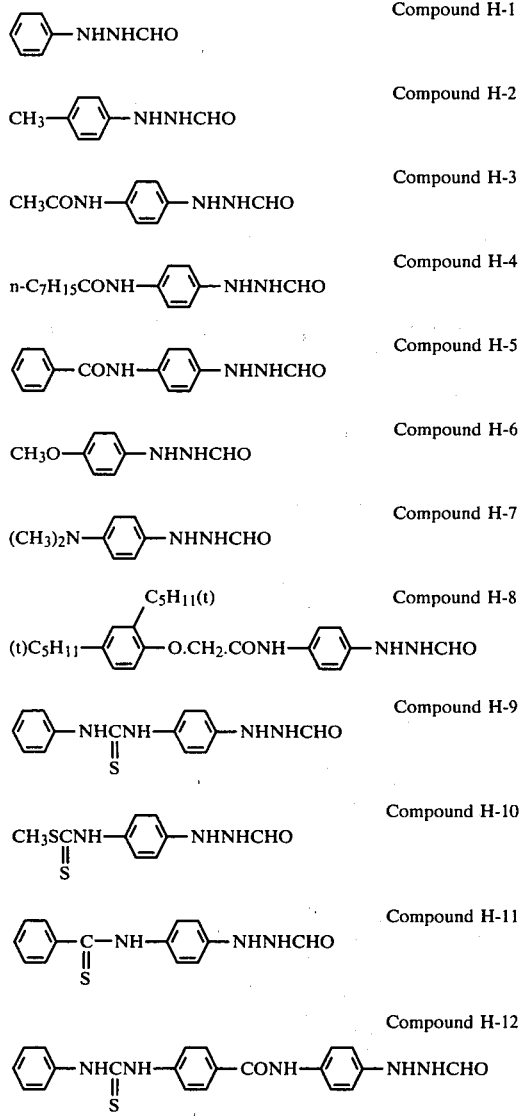

In methods (I) and (II) of this invention, exposure is performed as follows.

A variety of light sources can be employed for exposing the silver halide brought into contact with the spectral sensitizer. In any case, only light having a wavelength(s) that the spectral sensitizer alone absorbs is employed for exposure, excluding wave-length(s) in the absorption region intrinsic to silver halide. A suitable exposure degree is generally from $10^1$ to $10^{10}$ cms. As light sources, for example, a tungsten lamp, a halogen lamp, a mercury lamp, a xenon lamp, etc. can be employed in combination with a suitable optical filter (e.g., a sharp cut filter manufactured by Fuji Photo Film Co., Ltd.). In addition, a solid laser (e.g., a ruby laser, etc.), a semiconductor laser (e.g., a lead sulfide laser, etc.), a dye laser, a gas laser (e.g., a neon helium laser, an argon laser, etc.) and the like can be advantageously employed.

In this invention, it is preferred that when a transparent film (support) having the emulsion layer thereon is used, exposure be performed through the support to the emulsion layer. Upon exposure, it is necessary to employ a light source having overlaid thereon an optical filter to absorb light having wavelengths in the absorption region intrinsic to silver halide, or to use light from which wavelengths in the absorption region intrinsic to silver halide have been filtered out. It is particularly preferred that exposure be performed through a light source having overlaid thereon an optical filter which mainly transmits light of wavelengths that the spectral sensitizer absorbs.

The emulsion layer exposed as described above is then processed by conventional photographic processing. That is, in the case where the emulsion(s) is coated on a support, development processing techniques as are conventionally used for processing ordinary photographic films or printing paper can be utilized. Further, photographic processing can also be effected by developing, coating or spraying processing solutions on a support having coated thereon the emulsion(s), or dipping the support in processing solutions. Photo-grahic processing can also be performed by incorporating or mixing processing solutions into or with a liquid type emulsion.

When the hydrazine compound shown by formula (IX) is present for further enhancing detection sensitivity, development processing is performed in the presence of the hydrazine compound. More specifically, (1) the hydrazine compound is incorporated in at least one hydrophilic colloid layer(s) in the silver halide light sensitive layer-containing analysis element of this invention, or (2) the hydrazine compound is incorporated in a photographic pre-bath prior to development processing, a developer or a buffer solution employed for the immune reaction.

Needless to say, when the fogging agent is employed as the photographically active substance, the exposure step is omitted.

Subsequent development is carried out in a conventional manner as is well known in the art. Details of development conditions, developing agents, fixing, other processing compositions, etc. are described in copending U.S. application Ser. Nos. 126,919 and 126,920, both filed Mar. 3, 1980, which are incorporated herein by reference.

Having thus generally described this invention, the following working examples illustrate currently preferred modes of practicing this invention. In the following examples, percentages are all by weight, unless otherwise indicated.

EXAMPLE 1

Synthesis of insulin labelled with spectral sensitizer:

In 1 ml. of 4 mols of urea, 20 mg. of purified pork insulin (purchased from Sigma Chemicals Co., Ltd.) was dissolved. To the solution, 8 ml. of DMF (dimethyl formamide) was further added. The mixture was stirred under ice-cooling (0° to 4° C.) (Liquid A).

Spectral sensitizer (I)

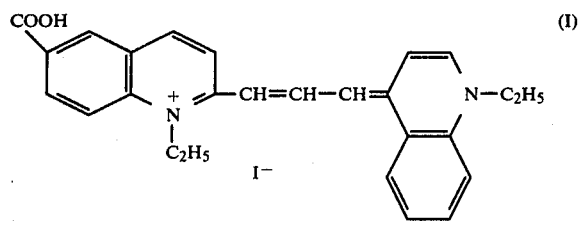

Spectral sensitizer (I) of the formula above (5 mg.) was dissolved in 2 ml. of DMF. Three sets of the solution were prepared under cooling at −15° to −20° C., 5 μl each of isobutyl chloroformate and 1.5 μl each of triethyl amine were added to the solutions, and 2 mg. each of hydroxysuccinimide was further added under still cooling (Liquid B).

Thereafter, Liquid B was added to Liquid A with stirring under ice-cooling (4° C.) and the mixture was reacted. After reacting for 30 mins. under ice-cooling and 30 mins. at room temperature, the reaction mixture was desalted with a Sephadex G-10 column equilibrated with 0.2 N ammonia water. Fractions containing sensitizer labelled insulin were collected and then lyophylized. Thus, insulin labelled with the spectral sensitizer was obtained; the thus labelled insulin was adsorbed on a silver chlorobromide emulsion to impart a maximum sensitivity thereto of around 685 nm; such also imparted a small maximum sensitivity at around 630 nm.

Preparation of silver chlorobromide emulsion

To 300 ml. of a 1% gelatin aqueous solution containing 49 g. of KBr and 17 g. of NaCl, 400 ml. of an aqueous solution of 100 g. of AgNO₃ was added at 70° C. After removing by-product (KNO₃, etc.), 5 g. of gelatin and 10 mg. of a chemical sensitizer (Na₂S₂O₃) were added to the mixture in a conventional manner and the mixture was then ripened in a conventional manner. Thus, about 1 kg. of silver chlorobromide emulsion (average grain size, 0.8μ) was obtained.

Composition of emulsion layer

A composition obtained by adding a small amount of a viscosity increases, a small amount of a stabilizer (6 ml. of 0.1% 1-phenyl-5-mercaptotetrazole) for the emulsion and a small amount of a coating aid per 100 g. of the silver chlorobromide emulsion.

Preparation of analysis sheet

Analysis sheets used in this example were prepared by coating, in succession, the silver chlorobromide emulsion described above, an auxiliary layer and a water-absorbing layer, on a cellulose triacetate support. Details are shown in Table 1, in which the auxiliary layer and the water absorbing layer were provided above and below the emulsion layer, respectively. Gelatin corresponding to a layer thickness of 10μ was further added to the emulsion layer of Sample No. 3 and to the water absorbing layer of Sample No. 6, 1 wt% of dimethyl urea was further added as a hardener based on the weight of polyvinyl alcohol.

TABLE 1

| Sample No. | Water Absorbing Layer composition | thickness | Emulsion Layer composition | thickness | Auxiliary Layer composition | thickness |
|---|---|---|---|---|---|---|
| 1 | none | — | AgX | | none | — |
| 2 | none | — | AgX | | gelatin | 10μ |
| 3 | none | — | AgX + gelatin | | none | — |
| 4 | gelatin | 10μ | AgX | | none | — |
| 5 | gelatin/vinyl pyrrolidone-acryl copolymer = 9/1 | 10μ | AgX | | none | — |
| 6 | polyvinyl alcohol | 10μ | AgX | | none | — |
| 7 | gelatin | 10μ | AgX | | gelatin | — |

*saponification degree, 88%

The insulin marked with the spectral sensitizer prepared as in Example 1 was dissolved in a tris-hydroxyaminomethane-hydrochloric acid buffer solution adjusted to pH 8.5, in a concentration of 1 ng/ml. The solution obtained was spotted in an amount of 25 μl each on Sample Nos. 1 to 7, together with 25 μl of the buffer solution containing no marked insulin, respectively. After allowing to stand for 10 mins., the analysis sheets were exposed using National Strobo PE-563 (made by Matsushita Electric Industries, Inc.) at a distance of 30 cm through SC-66 filter made by Fuji Photo Film Co., Ltd. Then the analysis sheet was developed with Developer A described below in the same manner as in Example 1 followed by fixing, washing with water and drying in a conventional manner. Black densities obtained on the analysis sheets were measured with a photographic densitometer made by Fuji Photo Film Co., Ltd. to calculate the difference in density from the blank.

Results are shown in Table 2 below.

TABLE 2

| | Sample No. | Optical Density |
|---|---|---|
| Comparison | 1 | 0.16 |
| | 2 | 0.14 |
| | 3 | 0.17 |
| This Invention | 4 | 0.78 |
| | 5 | 1.10 |
| | 6 | 0.85 |
| | 7 | 0.70 |

| Developer A: | |
|---|---|
| Metol | 0.31 g |
| Sodium hydrogen sulfite | 39.6 g |
| Hydroquinone | 6.0 g |
| Sodium carbonate (monohydrate) | 21.9 g |
| Potassium bromide | 0.86 g |
| Citric acid | 0.68 g |
| Potassium metabisulfite | 1.50 g |
| Water to make 1 liter | |

EXAMPLE 2

Sample Nos. 8 to 14 were prepared in a manner similar to Example 1 except that the layer thickness of the water absorbing layer was changed as shown in the table below in Sample Nos. 1 and 4 of Example I.

The same evaluation as in Examle 1 was performed.

Results are shown in Table 3.

TABLE 3

| Sample No. | Water Absorbing Layer | Difference in Optical Density |
|---|---|---|
| 8 |  | 0.15 |
| 9 | 0.5μ | 0.22 |
| 10 | 1μ | 0.31 |
| 11 | 5μ | 0.51 |
| 12 | 10μ | 0.75 |
| 13 | 20μ | 0.88 |
| 14 | 40μ | 0.90 |

From the results above, it is seen that the optical density detected can be increased with the increase thickness of the water absorbing layer; i.e., detection sensitivity can be improved.

EXAMPLE 3

Using Sample No. 5, the same measurement as in Example 1 was repeated nine times to examine if uneven density was observed. All of optical densities found were almost within the range of ±0.02 of the average optical density. That is, preferable results were obtained with reproducibility and stability of the assay by providing the water absorbing layer between the emulsion layer and the support.

EXAMPLE 4

Preparation of Glycylphenylalanyl amide modified with spectral sensitizer at the N terminal In 12.5 ml. of DMF, 131 mg. (250 μmole) of spectral sensitizer (II) described below was dissolved. The solution was then cooled to −15° C. and 33 μl (250 μmole) of isobutyl chloroformate was added thereto, Further, 35 μl (250 μmole) of triethyl amine was added to the resulting mixture followed by reaction at −15° to −10° C. for 5 mins. Thereafter, 70 mg (250 μmole) of glycylphenylalanyl amide acetate and 35 μl (250 μmole) of triethyl amine were added to the reaction mixture. The mixture was then further reacted at 0° C. for 1 hr. and at room temperature for 1 hr. To the reaction mixture, 25 ml of ethyl acetate was added. The precipitates formed were taken out by filtration and washed with ethyl acetate. The thus obtained powders were purified repeatedly by silica gel column chromatography (elute: chloroform/methanol = 3/1 by volume). Thereafter, recrystallization was performed from chloroform/methanol = 1/1 by volume to otain 128 mg (yield 71%) of the desired compound.

m.p. 199°–201° C.

$\lambda_{max}^{MeOH}$ ($\epsilon$) = 658 nm (1.80 × 10$^5$).

mass spectrum (FD) m/z = 600 (M-I).

Spectral sensitizer (II):

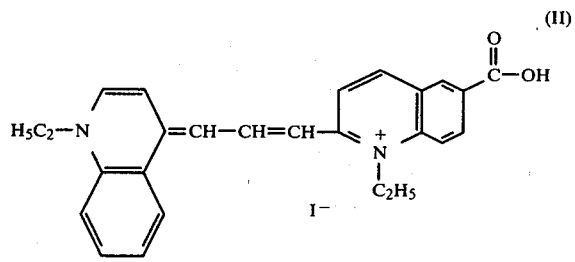

It was confirmed by TLC and UV and visible absorption spectra that this compound was hydrolyzed with β-D-galactosidase (made by Sigma Co., Ltd.) to release the compound:

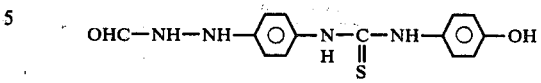

Next, using β-D-galactosidase obtained from E. coli and anti-α-fetoprotein rabbit IgG, an IgG-β-D-galactosidase conjugate was prepared using N,N'-o-phenylenedimaleimide. Further, anti-α-fetoprotein rabbit antibody was immobilized to glass beads having introduced therein amino groups, via glutaraldehyde, to prepare glass beads having immobilized thereto the anti-α-fetoprotein antibody (details are described in KOSO MENEKI SOKUTEIHO (Enzyme Immunoassay), edited by Eiji Ishikawa, et al., published by Igaku Shoin, 1978).

Using these anti-α-fetoprotein rabbit IgG-β-D-galactosidase, anti-α-fetoprotein rabbit IgG-immobilized glass beads (hereafter simply referred to as "glass beads") and Compound (II) described above, a calibration curve with standard α-fetoprotein solutions was prepared in accordance with the procedure described below.

In small test tubes in which a 0.1 M sodium phosphate buffer solution of pH 7.3 containing 0.15 M NaCl and 0.5% bovine serum albumin (Liquid A) was separately weighed in an amount of 0.4 ml. each, 0.1 ml. of standard α-fetoprotein solutions having various concentrations (5 to 160 ng/ml) prepared using Liquid A and 20 μl of horse serum were further weighed, respectively. Then a portion of the aforesaid glass beads having the antibody fixed thereto was added to the test tubes, respectively, and the mixtures were allowed to stand for 2 hrs. at 37° C. Thereafter, the reaction liquids were removed using an aspirator, and 1 ml. of a 0.01 M sodium phosphate buffer solution (pH 7.5) containing 0.1 M NaCl and 1 mM MgCl$_2$ and 0.1% BSA (Liquid B) was added to the residues to wash them twice. After washing, 0.2 ml. of an anti-α-fetoprotein antibody-β-D-galactosidase conjugate prepared using Liquid B was added and the mixtures were again allowed to stand for 2 hrs. at 37° C. Dilution of the conjugate was performed in such a manner that 160 ng/ml of standard α-fetoprotein indicated black density after development described below of 2.0 to 2.5. Then, after the reaction liquids were removed, 1 ml. of Liquid B was again added to the residues to wash them twice. Then, 0.5 ml. of a 0.1% of the synthetic substrate dissolved in Liq. B was added and the mixtures were allowed to stand for 1 hr. at 37° C. Each of the reaction liquids was separately passed through a silica gel column of 3 mmφ × 15 mm (chloroform-methanol) to isolate the reaction product. After evaporating off the solvent, the reaction product was dissolved in 0.2 ml. of Liquid B and the resulting solution was dropped onto the films of Sample Nos. 8 and 11 obtained in Example 2. Thereafter the same procedure as in Example 1 was repeated and the measurement was carried out.

Optical densities of the blackened areas are shown in Table 4 below.

TABLE 4

| Concentration of Standard Insulin (ng/ml) | Black Density | |
| --- | --- | --- |
| | Sample No. 8 (comparison) | Sample No. 11 (invention) |
| 0 | 0.18 | 0.20 |
| 2.5 | 0.19 | 0.51 |
| 5.0 | 0.27 | 0.85 |
| 10.0 | 0.55 | 1.20 |
| 20.0 | 0.90 | 1.54 |
| 40.0 | 1.24 | 1.88 |
| 80.0 | 1.58 | 2.20 |
| 160.0 | 1.93 | 2.55 |

As is seen from the results above, the analysis sheet (Sample No. 11) having the water absorbing layer provided higher sensitivity than Sample No. 8 having no water absorbing layer, and also gave a good calibration curve.

While the invention has been described in detail and with reference to specific embodiments thereof, it will be apparent from one skilled in the art that various changes and modifications can be made therein without departing from the spirit and scope thereof.

What is claimed is:

1. In an analysis element, comprising a support having provided thereon a silver halide emulsion layer, for immunochemical assay of a trace component utilizing an immunological reaction which comprises: (1) labelling an antigen or antibody with a photographically active substance selected from the group consisting of a spectral sensitizer and a fogging agent, (2) competitively reacting said antigen or antibody labelled with said photographically active substance with an antibody or antigen which specifically reacts with the respective antigen or antibody, (3) bringing either the reaction product or the unreacted material into contact with said silver halide, (4) exposing the resulting product to light having a wavelength which said photographically active substance absorbs followed by photographic development when said spectral sensitizer is used as said photographically active substance, or developing the same without exposure to light having a wavelength which said photographically active substance absorbs when said fogging agent is used as said photographically active substance, and (5) measuring the resulting optical density of the formed silver image and/or colored dye, the improvement which comprises a water absorbing layer is provided between said support and said silver halide emulsion layer, wherein said water absorbing layer has a thickness of from 1 to 100µ and is composed of a porous membrane, a filter paper, a fiber or a binder comprising gelatin and/or a polymer.

2. In an analysis element, comprising a support having provided thereon a silver halide emulsion layer, for assay of an enzyme activity and/or a quantity of an enzyme which comprises: (1) using a synthetic substrate comprising at least one structure ① which is catalytically affected by an enzyme to be assayed and at least one photographically active substance structure ② selected from the class consisting of a spectral sensitizer and a fogging agent in the molecule thereof, (2) bringing either the reaction product formed by enzyme reaction or the unreacted synthetic substrate into contact with silver halide, (3) exposing the same to light having a wavelength which said photographically active substance absorbs followed by development when said spectral sensitizer is used as said photographically active substance, or developing the same without exposure to light when said fogging agent is used as said photographically active substance, and (4) measuring optical density of the formed silver image and/or colored dye, the improvement which comprises a water absorbing layer is provided between said support and said silver halide emulsion layer, wherein said water absorbing layer has a thickness of from 1 to 100µ and is composed of a porous membrane, a filter paper, a fiber or a binder comprising gelatin and/or a polymer.

3. The analysis element as in claim 2 wherein said at least ① structure is catalytically cleaved by said enzyme.

* * * * *